US012148530B2

(12) United States Patent
Moturu et al.

(10) Patent No.: US 12,148,530 B2
(45) Date of Patent: Nov. 19, 2024

(54) METHOD FOR PROVIDING PATIENT INDICATIONS TO AN ENTITY

(71) Applicant: OrangeDot, Inc., Santa Monica, CA (US)

(72) Inventors: Sai Moturu, San Francisco, CA (US); Anmol Madan, San Francisco, CA (US); Shishir Dash, San Francisco, CA (US); Karim Wahba, San Francisco, CA (US)

(73) Assignee: OrangeDot, Inc., Santa Monica, CA (US)

( * ) Notice: Subject to any disclaimer, the term of this patent is extended or adjusted under 35 U.S.C. 154(b) by 398 days.

(21) Appl. No.: 16/919,775

(22) Filed: Jul. 2, 2020

(65) Prior Publication Data
US 2020/0402626 A1 Dec. 24, 2020

Related U.S. Application Data

(63) Continuation of application No. 15/069,163, filed on Mar. 14, 2016, now Pat. No. 10,748,645, which is a
(Continued)

(51) Int. Cl.
*G16H 50/20* (2018.01)
*G16H 10/60* (2018.01)
(Continued)

(52) U.S. Cl.
CPC ............ *G16H 50/20* (2018.01); *G16H 10/60* (2018.01); *G16H 50/30* (2018.01); *G16H 50/50* (2018.01);
(Continued)

(58) Field of Classification Search
CPC ........ G16H 50/20; G16H 10/60; G16H 50/30; G16H 50/50; G16H 10/20; G16H 40/63; G16H 50/70
See application file for complete search history.

(56) References Cited

U.S. PATENT DOCUMENTS

| | | |
|---|---|---|
| 4,845,323 A | 7/1989 | Beggs |
| 6,356,940 B1 | 3/2002 | Short |

(Continued)

FOREIGN PATENT DOCUMENTS

| | | |
|---|---|---|
| CN | 101600008 A | 12/2009 |
| DE | 102016101665 A1 | 8/2016 |

(Continued)

OTHER PUBLICATIONS

Calvo, et al., "Natural language processing in mental health applications using non-clinical texts", Natural Language Engineering 23 (5): 649-685. © Cambridge University Press 2017. (Year: 2017).

(Continued)

*Primary Examiner* — Chad A Newton
(74) *Attorney, Agent, or Firm* — Jeffrey Schox

(57) ABSTRACT

A method and system for providing patient indications to an entity, the method comprising: for each of a set of patients: by way of an application executing at a mobile computing device, accessing a sensor system and a log of use of a communication application executing on the mobile computing device; receiving a survey response dataset; generating a behavioral dataset, derived from the sensor system and the log of use; generating a predictive model derived from at least one of the survey response dataset and the behavioral dataset; generating comparisons of outputs of blocks of the method to threshold conditions; producing a set of indications corresponding to the set of patients, derived from generation of, for each of the set of patients, an indication in response to the comparisons; and transmitting a portion of the set of indications to the entity according to a resource constraint of the entity.

19 Claims, 13 Drawing Sheets

Related U.S. Application Data continuation-in-part of application No. 13/969,339, filed on Aug. 16, 2013, now abandoned.

(60) Provisional application No. 61/683,867, filed on Aug. 16, 2012, provisional application No. 61/683,869, filed on Aug. 16, 2012, provisional application No. 62/132,912, filed on Mar. 13, 2015, provisional application No. 62/172,566, filed on Jun. 8, 2015.

(51) Int. Cl.
| | | |
|---|---|---|
| *G16H 50/30* | (2018.01) | |
| *G16H 50/50* | (2018.01) | |
| *G16H 10/20* | (2018.01) | |
| *G16H 40/63* | (2018.01) | |
| *G16H 50/70* | (2018.01) | |

(52) U.S. Cl.
CPC ............ *G16H 10/20* (2018.01); *G16H 40/63* (2018.01); *G16H 50/70* (2018.01)

(56) References Cited

U.S. PATENT DOCUMENTS

| | | | |
|---|---|---|---|
| 6,827,670 | B1 | 12/2004 | Stark et al. |
| 7,188,151 | B2 | 3/2007 | Kumar et al. |
| 7,246,677 | B2 | 7/2007 | Fredriksson et al. |
| 7,248,677 | B2 | 7/2007 | Randall et al. |
| 7,337,158 | B2 | 2/2008 | Fratkina et al. |
| 7,376,700 | B1 | 5/2008 | Clark et al. |
| 7,395,216 | B2 | 7/2008 | Rosenfeld et al. |
| 7,584,166 | B2 | 9/2009 | Grichnik |
| 7,761,309 | B2 | 7/2010 | Sacco et al. |
| 7,818,185 | B2 | 10/2010 | Bjorner et al. |
| 7,912,528 | B2 | 3/2011 | Krishnan et al. |
| 7,914,468 | B2 | 3/2011 | Shalon et al. |
| 8,160,901 | B2 | 4/2012 | Heywood et al. |
| 8,265,955 | B2 | 9/2012 | Michelson et al. |
| 8,398,538 | B2 | 3/2013 | Dothie et al. |
| 8,423,387 | B1 | 4/2013 | Mirza |
| 8,488,761 | B2 | 7/2013 | Reding et al. |
| 8,500,635 | B2 | 8/2013 | Zilca et al. |
| 8,622,900 | B2 | 1/2014 | Jain et al. |
| 8,655,817 | B2 | 2/2014 | Hasey et al. |
| 8,684,922 | B2 | 4/2014 | Tran |
| 8,726,195 | B2 | 5/2014 | Bill |
| 8,781,102 | B2 | 7/2014 | Conway et al. |
| 8,977,248 | B1 | 3/2015 | Bladon et al. |
| 9,019,106 | B2 | 4/2015 | Alameh et al. |
| 9,116,669 | B2 | 8/2015 | Desai et al. |
| 9,195,948 | B2 | 11/2015 | Son et al. |
| 9,286,442 | B2 | 3/2016 | Csoma et al. |
| 9,294,403 | B2 | 3/2016 | Mejia et al. |
| 9,497,585 | B1 | 11/2016 | Cooley et al. |
| 9,684,922 | B2 | 6/2017 | Elberbaum |
| 9,713,724 | B2 | 7/2017 | Petersen et al. |
| 9,754,220 | B1 | 9/2017 | Brestoff et al. |
| 9,763,592 | B2 | 9/2017 | Le et al. |
| 10,068,670 | B2 | 9/2018 | Moturu et al. |
| 10,095,992 | B1 | 10/2018 | Brestoff et al. |
| 10,276,260 | B2 | 4/2019 | Moturu et al. |
| 10,741,285 | B2 | 8/2020 | Moturu et al. |
| 10,748,645 | B2 | 8/2020 | Moturu et al. |
| 10,812,424 | B1 | 10/2020 | Bommaraju et al. |
| 11,710,576 | B2 | 7/2023 | Shah |
| 2002/0198473 | A1 | 12/2002 | Kumar et al. |
| 2003/0119794 | A1 | 6/2003 | Bacaner et al. |
| 2004/0078223 | A1 | 4/2004 | Sacco et al. |
| 2004/0122702 | A1 | 6/2004 | Sabol et al. |
| 2004/0122703 | A1 | 6/2004 | Walker et al. |
| 2004/0143453 | A1 | 7/2004 | Weaver |
| 2004/0199401 | A1 | 10/2004 | Wagner et al. |
| 2004/0210153 | A1 | 10/2004 | Tsukashima et al. |
| 2004/0225340 | A1 | 11/2004 | Evans |
| 2005/0020903 | A1 | 1/2005 | Krishnan et al. |
| 2005/0055321 | A1 | 3/2005 | Fratkina et al. |
| 2005/0069936 | A1 | 3/2005 | Diamond et al. |
| 2005/0080462 | A1* | 4/2005 | Jenkins .................. G16H 20/60 607/58 |
| 2005/0108051 | A1 | 5/2005 | Weinstein |
| 2005/0169446 | A1 | 8/2005 | Randall et al. |
| 2006/0064037 | A1 | 3/2006 | Shalon et al. |
| 2007/0022612 | A1 | 2/2007 | Perrin |
| 2007/0094048 | A1 | 4/2007 | Grichnik |
| 2007/0226012 | A1 | 9/2007 | Salgado et al. |
| 2007/0288266 | A1 | 12/2007 | Sysko et al. |
| 2008/0059570 | A1 | 3/2008 | Bill |
| 2008/0061125 | A1 | 3/2008 | Langlois et al. |
| 2008/0201429 | A1 | 8/2008 | Barbell et al. |
| 2009/0125333 | A1 | 5/2009 | Heywood et al. |
| 2009/0161907 | A1 | 6/2009 | Healey et al. |
| 2009/0247834 | A1 | 10/2009 | Schechter |
| 2010/0082367 | A1 | 4/2010 | Hains et al. |
| 2010/0179833 | A1 | 7/2010 | Roizen et al. |
| 2010/0198614 | A1 | 8/2010 | Chopra et al. |
| 2010/0203876 | A1 | 8/2010 | Krishnaswamy |
| 2010/0280838 | A1 | 11/2010 | Bosworth et al. |
| 2010/0325588 | A1* | 12/2010 | Reddy .................. H04L 63/0263 706/12 |
| 2011/0009715 | A1 | 1/2011 | O et al. |
| 2011/0015467 | A1 | 1/2011 | Dothie et al. |
| 2011/0066036 | A1 | 3/2011 | Zilca et al. |
| 2011/0082712 | A1 | 4/2011 | Eberhardt et al. |
| 2011/0118555 | A1 | 5/2011 | Dhumne et al. |
| 2011/0119212 | A1 | 5/2011 | De et al. |
| 2011/0125238 | A1 | 5/2011 | Nofzinger |
| 2011/0161110 | A1 | 6/2011 | Mault |
| 2011/0184250 | A1 | 7/2011 | Schmidt et al. |
| 2011/0245633 | A1 | 10/2011 | Goldberg et al. |
| 2011/0295621 | A1 | 12/2011 | Farooq et al. |
| 2011/0306028 | A1 | 12/2011 | Galimore |
| 2011/0314558 | A1 | 12/2011 | Song et al. |
| 2012/0016218 | A1 | 1/2012 | Lau et al. |
| 2012/0041786 | A1* | 2/2012 | Yu ........................ G16H 40/67 705/3 |
| 2012/0053425 | A1 | 3/2012 | Michelson et al. |
| 2012/0131183 | A1* | 5/2012 | Heidt .................... H04W 12/02 709/224 |
| 2012/0143013 | A1 | 6/2012 | Davis et al. |
| 2012/0179480 | A1* | 7/2012 | Patel ...................... G16H 10/20 705/2 |
| 2012/0203545 | A1 | 8/2012 | Shaw |
| 2012/0221357 | A1* | 8/2012 | Krause .................... H04L 51/52 705/4 |
| 2012/0238936 | A1* | 9/2012 | Hyde .................... A61B 5/1459 604/8 |
| 2012/0289791 | A1 | 11/2012 | Jain et al. |
| 2013/0004129 | A1 | 1/2013 | Zhang |
| 2013/0041290 | A1* | 2/2013 | Kording .................. A61B 5/117 600/595 |
| 2013/0042116 | A1 | 2/2013 | Sakumoto |
| 2013/0060580 | A1 | 3/2013 | Chapman et al. |
| 2013/0085758 | A1 | 4/2013 | Csoma et al. |
| 2013/0085773 | A1 | 4/2013 | Yao et al. |
| 2013/0095459 | A1 | 4/2013 | Tran |
| 2013/0117040 | A1 | 5/2013 | James et al. |
| 2013/0154838 | A1 | 6/2013 | Alameh et al. |
| 2013/0179178 | A1 | 7/2013 | Vemireddy et al. |
| 2013/0246330 | A1 | 9/2013 | Son et al. |
| 2013/0297536 | A1 | 11/2013 | Almosni et al. |
| 2013/0324861 | A1 | 12/2013 | Ando et al. |
| 2014/0019161 | A1 | 1/2014 | Op Den Buijs et al. |
| 2014/0039907 | A1 | 2/2014 | Schaefer et al. |
| 2014/0039914 | A1 | 2/2014 | Dansereau et al. |
| 2014/0052465 | A1 | 2/2014 | Madan et al. |
| 2014/0052474 | A1 | 2/2014 | Madan et al. |
| 2014/0257439 | A1 | 9/2014 | Douglas |
| 2015/0003247 | A1 | 1/2015 | Mejia et al. |
| 2015/0187199 | A1 | 7/2015 | Chang et al. |
| 2015/0310606 | A1 | 10/2015 | Shreve et al. |
| 2015/0332012 | A1 | 11/2015 | Edelson et al. |
| 2015/0370994 | A1 | 12/2015 | Madan et al. |
| 2016/0292862 | A1 | 10/2016 | Mask |

(56) References Cited

U.S. PATENT DOCUMENTS

| | | |
|---|---|---|
| 2016/0317781 A1 | 11/2016 | Proud |
| 2017/0124643 A1 | 5/2017 | Haimi et al. |
| 2018/0083903 A1 | 3/2018 | El-Alfy et al. |
| 2018/0089449 A1 | 3/2018 | Boudreau et al. |
| 2018/0333106 A1 | 11/2018 | Roberts et al. |
| 2018/0374046 A1 | 12/2018 | Powers et al. |
| 2019/0042699 A1 | 2/2019 | Bastide et al. |
| 2019/0197097 A1 | 6/2019 | Nagarajan et al. |
| 2020/0242566 A1 | 7/2020 | Agarwal et al. |
| 2021/0090733 A1 | 3/2021 | Dibari et al. |
| 2021/0249137 A1 | 8/2021 | Dil Nahlieli |
| 2021/0390625 A1 | 12/2021 | Hayes et al. |
| 2022/0061746 A1 | 3/2022 | Lyman et al. |
| 2022/0093253 A1 | 3/2022 | Misrilall et al. |
| 2022/0285032 A1 | 9/2022 | Covington et al. |
| 2022/0301152 A1 | 9/2022 | Yim et al. |

FOREIGN PATENT DOCUMENTS

| | | |
|---|---|---|
| EP | 2667313 A2 | 11/2013 |
| JP | 2003339674 | 12/2003 |
| JP | 2010514497 A | 5/2010 |
| WO | 02067122 A1 | 8/2002 |
| WO | 2008085308 A1 | 7/2008 |
| WO | 2008096634 A1 | 8/2008 |
| WO | 2012025622 A2 | 3/2012 |
| WO | 2013042116 A1 | 3/2013 |
| WO | 2015003247 A1 | 1/2015 |
| WO | 2020201077 A1 | 10/2020 |

OTHER PUBLICATIONS

Coppersmith, et al., "Natural Language Processing of Social Media as Screening for Suicide Risk", Biomedical Informatics Insights vol. 10: 1-11 © The Author(s) 2018. (Year: 2018).

Ji, et al., "Supervised Learning for Suicidal Ideation Detection in Online User Content", Hindawi Complexity vol. 2018, Article ID 6157249, 10 pages https://doi.org/10.1155/2018/6157249. (Year: 2018).

Skaik, et al., "Using Social Media for Mental Health Surveillance: A Review", ACM Comput. Surv. 53, 6, Article 129 (Dec. 2020 ), 31 pages. https://doi.org/10.1145/3422824. (Year: 2020).

"Major Virginia Smith; et al. 'Work Time Interference With Family, and Psychological Distress' 2002, Journal of Applied Psychology, vol. 87, No. 3, 427-436 (Year: 2002)", Jan. 11, 2018 00:00:00.0.

"Pifzer, Patient Health Questionnaire (PH-9)", Pfizer Non-Patent Literature, 1999, pp. 1 and 2.

Thomee, Sara, et al., "Mobile phone use and stress, sleep disturbances, and symptoms of depression among young adults—a prospective short study", BMC Public Health, Biomed Central, London, GB, vol. 11, No. 1, Jan. 31, 2011, p. 66.

Yen, Cheng-Fang, et al., "Symptoms of problematic cellular phone use, functional impairment and its association with depression among adolescents in Southern Taiwan", Journal of Adolescence, Academic Press, Amsterdam, NL, vol. 32, No. 4, Aug. 1, 2009, pp. 863-873.

\* cited by examiner

| Coach C Online | | | | |
|---|---|---|---|---|
| Current | Outreach | Remind | | All |
| ID ⇕Suicidal | ⇕Outreach | ⇕Messages | ⇵Last Msg | ▲Call |
| 934  1 | P1 | 3 | Now | ☎ |
| 1275*  2 | P2 | 2 | 13m | ☎ |
| 346 | | 1 | 67m | ☎ |
| 761*  1 | P3 | | 2h | ☎ |

Suicidal: Suicidal Ideation
Outreach: Outreach Priority
Messages: Unread message count
Last Msg: Time since last message
*: Active reminder for outreach

FIGURE 3F

| Coach C Online | | | | |
|---|---|---|---|---|
| Current | Outreach | Remind | | All |
| ID ⇕Suicidal | ⇕Outreach | ⇕Messages | ⇵Last Msg | ▲Call |
| 934  1 | P1 ➜ | PHQ-9 Increase | 7 | ☎ |
| 1275*  2 | P2 | PHQ-9 Score | 23 | ☎ |
| 346 | | Date | 3 days ago | ☎ |
| 761*  1 | P3 | | 2h | ☎ |

Suicidal: Suicidal Ideation
Outreach: Outreach Priority
Messages: Unread message count
Last Msg: Time since last message
*: Active reminder for outreach

FIGURE 3G

934: Samantha, Female, 33

Chat Window
Hello coach
How can I help you today?
I am having a stressfull time at work again
I am sorry to hear that
Did you try the mindfulness exercise?
It was helpful last time
But it is hard to practice in the office

[ Coach shares an exercise > ]
Try this exercise today

Message Window
It should be easy to practice in the office_

↪ Share content  ☐ Outreach complete
📄 Send survey  🗄 Archive chat
📅 Add reminder

CHAT VIEW

---

TEARAWAY NOTES [+]

DATA REPORT [+]

---

934: Samantha, Female, 33

Chat Window
Hello coach
How can I help you today?
I am having a stressfull time at work again
I am sorry to hear that
Did you try the mindfulness exercise?

Content Library

[🔍 search]

| Emotional symptoms ▼ |
|---|
| Depressed mood |
| Anxiety |
| Lack of enjoyment |
| Guild and negative thoughts |
| Loneliness |

Physica...
Se...

Relationships ▽

Tough situations ▽

CHAT VIEW

---

934: Samantha, Female, 33

Chat Window
Hello coach
How can I help you today?
I am having a stressfull time at work again
I am sorry to hear that
Did you try the mindfulness exercise?

Content Library

[🔍 search]

◀ Emotional symptoms > Anxiety

| Tip 1 |
| Description | ➡ |

| Exercise 1 |
| Description | ➡ |

| Tip 2 |
| Description | ➡ |

CHAT VIEW

FIGURE 3H

TEARAWAY NOTES [−]

📄 Documentation    ⌃ Escalate    ↪ Handoff

| Reminders | Goals & Notes | Context |
|---|---|---|
| Tue - F/U on share tip use | Help with problems at work | Diagnosis: Depressed (3 months) |
| Fri - F/U on conversation with boss | Make sleep schedule consistent | Trigger: Job performance review |
| Future - Share negative thoughts exercises | Communication - Prefers regular check-in every 2 or 3 days | Meds: Prozac<br>Therapist: Gingerio ID 3482 |

DATA REPORT [−]

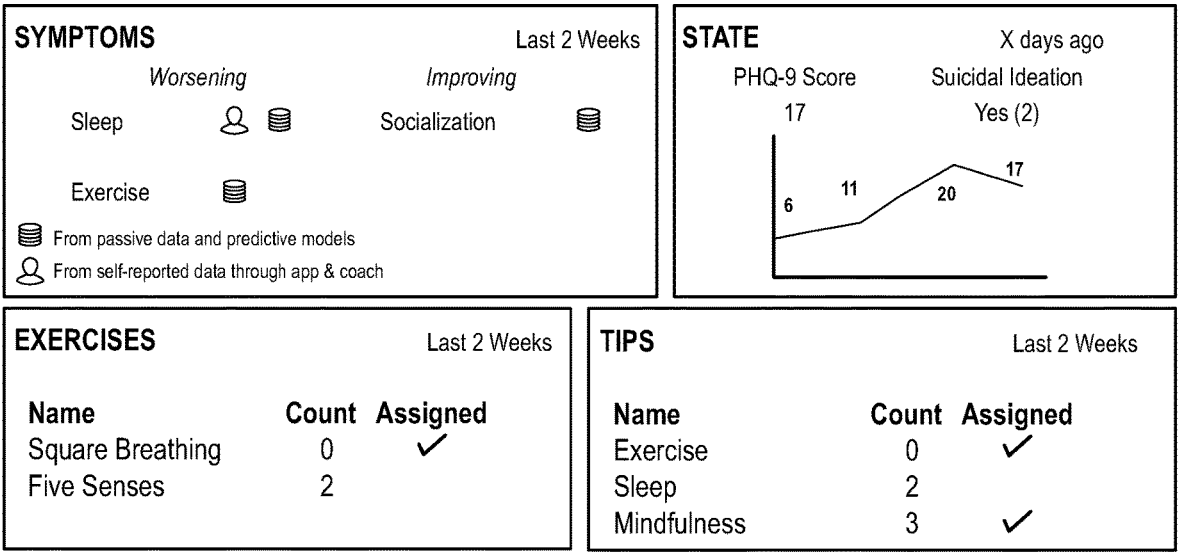

DATA VIEW

FIGURE 3I

1. TRIGGERS

2. TRENDS

3. VISUALIZATIONS

METHOD FOR PROVIDING PATIENT INDICATIONS TO AN ENTITY

CROSS-REFERENCE TO RELATED APPLICATIONS

This application is a continuation of Ser. No. 15/069,163 filed 14 Mar. 2016, which is a continuation-in-part application of U.S. application Ser. No. 13/969,339 filed 16 Aug. 2013, which claims the benefit of U.S. Provisional Application Ser. No. 61/683,867 filed on 16 Aug. 2012 and U.S. Provisional Application Ser. No. 61/683,869 filed on 16 Aug. 2012, which are each incorporated in its entirety herein by this reference.

This application is also related to U.S. application Ser. No. 15/005,923 filed 25 Jan. 2016, which is incorporated in its entirety herein by this reference.

This application is a continuation of Ser. No. 15/69,163 filed 14 Mar. 2016 which also claims the benefit of U.S. Provisional Application Ser. No. 62/132,912 filed 13 Mar. 2015 and U.S. Provisional Application Ser. No. 62/172,566 filed 8 Jun. 2015, which are each incorporated in its entirety herein by this reference.

TECHNICAL FIELD

This invention relates generally to the field of healthcare and more specifically to a new and useful method for providing patient indications to an entity in the healthcare field.

BACKGROUND

Life event triggers and other factors contributing to adverse psychological and/or physiological states can result in a combination of symptoms that interfere with a person's ability to work, sleep, study, eat, and enjoy once-pleasurable activities. For some individuals diagnosed with a disorder or a condition, access to therapy is limited, and the processes of receiving appropriate forms of therapy are often fraught with unnecessary inefficiencies. Timely/early intervention in many forms of disease progression is crucial to affecting patient outcomes; however, timely intervention requires intensive patient assessment and monitoring. Current systems and methods for monitoring patients exhibiting symptoms of conditions that affect psychological and/or physical states can influence patient outcomes, but are typically time intensive, cost-intensive, and/or entirely fail to identify when a patient is entering a critical state of a condition at which intervention would be most effective. Furthermore, current systems and methods are ineffective at optimizing patient treatment, in a manner that takes workflow issues (e.g., volume of workflow, distribution of workflow) for healthcare providers into account. As such, current standards of detection, diagnosis and treatment of many disorders and conditions, as well as barriers (e.g., social barriers) to seeking diagnosis and treatment, are responsible for delays in diagnoses of disorders and/or misdiagnoses of disorders, which cause such disorders and conditions to remain untreated. Furthermore, such standards result in a reactionary approach, as opposed to a preventative approach to a critical event. In addition to these deficiencies, further limitations in detection, diagnosis, treatment, and/or monitoring of patient progress during treatment prevent adequate care of patients with diagnosable and treatable conditions.

As such, there is a need in the field of healthcare for a new and useful method and system for providing patient indications to an entity in the healthcare field. This invention creates such a new and useful and system.

BRIEF DESCRIPTION OF THE FIGURES

FIGS. 3F-3I depict example tools for providing indications in an embodiment of a method for providing patient indications to an entity;

DESCRIPTION OF THE EMBODIMENTS

The following description of the embodiments of the invention is not intended to limit the invention to these embodiments, but rather to enable any person skilled in the art to make and use this invention.

1. Method

Figure 1A:
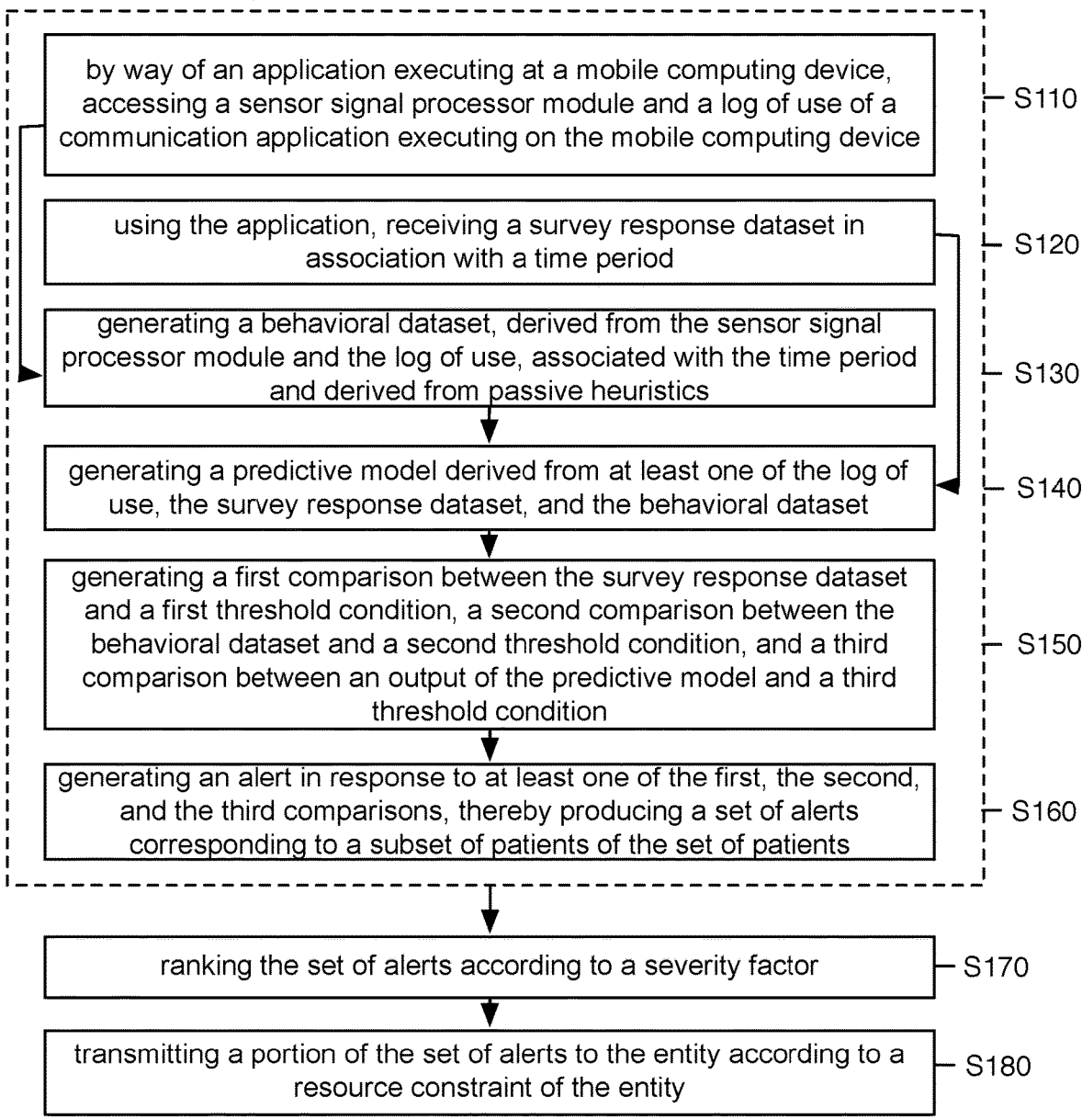
FIGS. 1A and 1B are flowcharts of portions of an embodiment of a method for providing patient indications to an entity.
Figure 1B:
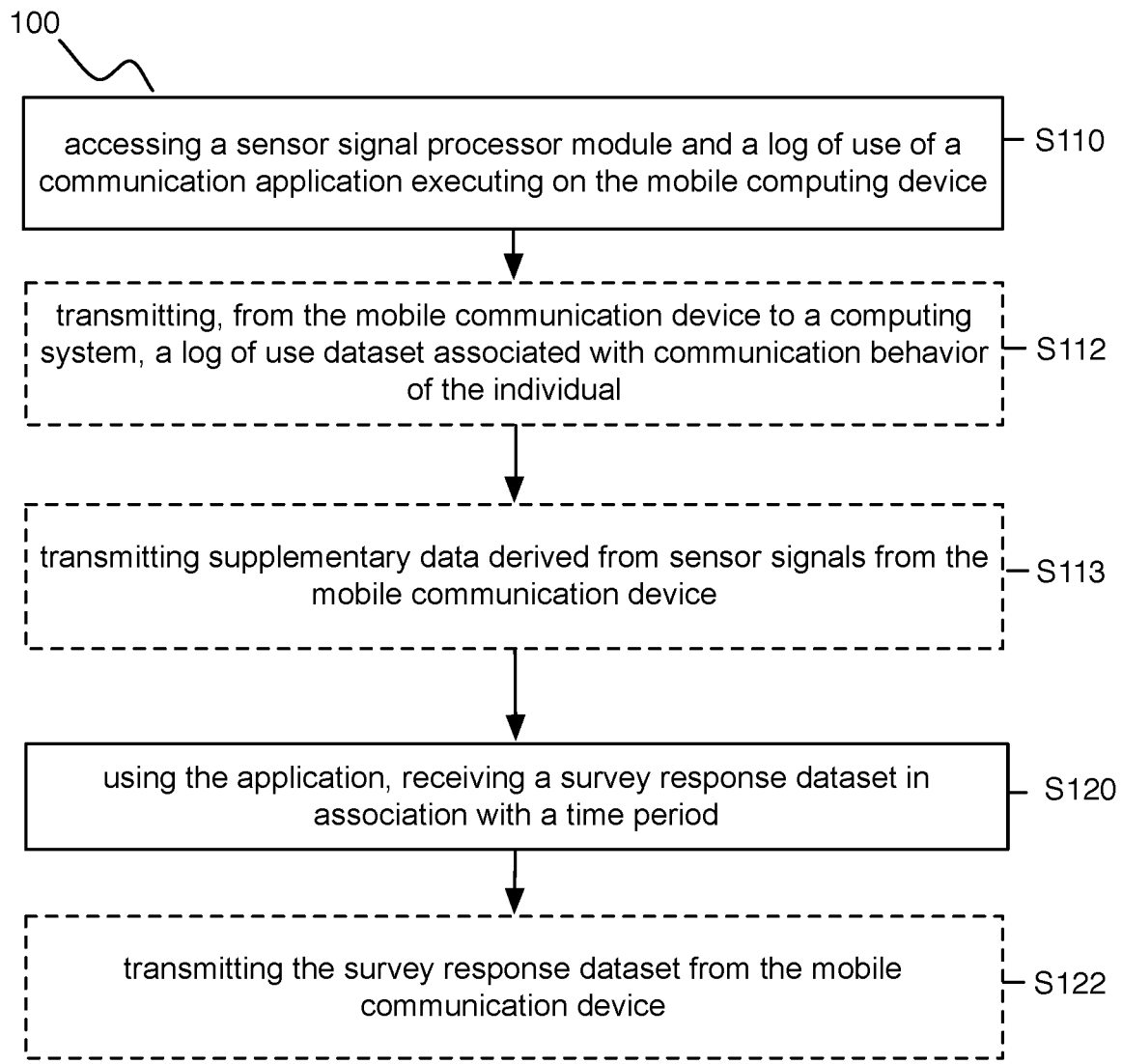

As shown in FIGS. 1A and 1B, a method 100 for providing patient indications to an entity comprises: for each of a set of patients: by way of an application executing at a mobile computing device, accessing a sensor signal processor module and a log of use of a communication application executing on the mobile computing device Silo; using the application, receiving a survey response dataset in association with a time period S120; generating a behavioral dataset, derived from the sensor signal processor module and the log of use, associated with the time period and derived from passive behavior S130; generating a predictive model derived from at least one of the log of use, the survey response dataset, and the behavioral dataset S140; generating a first comparison between the survey response dataset and a first threshold condition, a second comparison between the behavioral dataset and a second threshold condition, and a third comparison between an output of the predictive model and a third threshold condition S150; and generating an indication in response to at least one of the first, the second, and the third comparisons, thereby producing a set of indications corresponding to a subset of patients of the set of patients S160; ranking the set of indications according to a severity factor S170; and transmitting a portion of the set of indications to the entity according to a resource constraint of the entity S180.

The method 100 functions to generate and provide indications pertaining to a population of patients, in a manner that improves indication provision effectiveness (e.g., with regard to a patient being symptomatic, with regard to detection prior to a patient entering a critical state, etc.), and takes into account resource constraints (e.g., human resource limitations, workflow volume, workflow distribution, workflow timing, intervention cost, etc.). As such, the method 100 can contribute to improved efficiency in handling patients by enhancing delivery of patient-related indications to a healthcare provider, reducing volume of patient-related indications to the healthcare provider, and providing improved patient outcomes through an improved assessment of patient states of need.

1.1 Benefits

In variations and examples, the method 100 can confer several benefits over conventional methodologies for managing health of a population of patient, some of which are provided below.

For instance, in some applications, the method 100 can be used to create alerts/triggers pertaining to a population of patients or other grouping of patients associated with an entity (e.g., therapeutic entity, coaching entity, etc.), wherein the alerts/triggers can be generated based upon heuristic methods, self-reported data acquisition methods, and/or any other suitable methods, in order to identify trends and/or aberrations in behavior for multiple patients using unconventional methods. In more detail, blocks of the method 100 can be used to monitor one or more users interacting with a mobile device application platform, in order to enable detection of aberrant behaviors or other deviations from patterns in behavior, wherein such behaviors are indicative of changes in health state (e.g., mental health state). As such, detection of aberrant behaviors or other deviations from patterns in behavior, as enabled by the method 100, can be used to appropriately intervene in manners that improve health states of users.

The method 100 can additionally or alternatively be used to predict and/or interpret an overall state of the individual or to predict and/or interpret states of individual symptoms of an individual using unconventional data sources and methods. Furthermore, embodiments of the method 100 can be used to characterize statuses of patients at instances in time, or to characterize changes in status of patients over time. As described in more detail below, variations of the method 100 can implement computational methods for processing sensor, communication, and survey data, generating predictive models, and iteratively refining predictive models, in order to facilitate monitoring of a patient population in the short and long term. The method 100 can thus provide an entity with guidance for intervening on behalf of one or more patients (e.g., in terms of active outreach, in terms of elevating care of at-risk patients), and can provide a patient with content (e.g., information, activities) configured to promote health of the patient.

In generating the indications, the method 100 preferably processes survey responses, communication behavior, mobility behavior, and any other suitable supplementary information in order to determine the appropriate time(s) to provide indications pertaining to one or more patients, as well as the format(s) of provided indications. In variations, the method 100 can facilitate monitoring of states of a disorder or condition (e.g., a psychological disorder, a condition of depression, a pain-related condition, a sleep-related condition, a cardiovascular disease related condition, etc.), by enabling detection of changes in the patient's condition. In a specific application, the method 100 can monitor and analyze communication behavior, mobility behavior, and/or other behavior detected from any other suitable sensor(s) associated with a population of patients over time, and provide indications pertaining to a caretaker associated with the population of patients based upon severity of the condition of each patient. Thus, the method 100 can provide mechanism for multiple patients to achieve appropriate interventions, in a manner that accounts for indication frequency (e.g., per patient, for a population of patients), resource constraints, precision in timing of indications, and intervention goals. Furthermore, the indication(s) generated by the method 100 can be used to drive one or more interventions (e.g., interventions delivered through an application executing on a mobile computing device, health advice electronically delivered to a patient, elements of a therapy program electronically delivered to a patient, etc.). In particular, the intervention(s) delivered to a patient can further be based upon contextual information (e.g., a location of the patient, an assessment of "free time of the patient" based upon the patient's location/schedule/mobile device usage, etc.) pertaining to the patient. However, the method 100 can additionally or alternatively be implemented for any other suitable application.

Figure 1C:
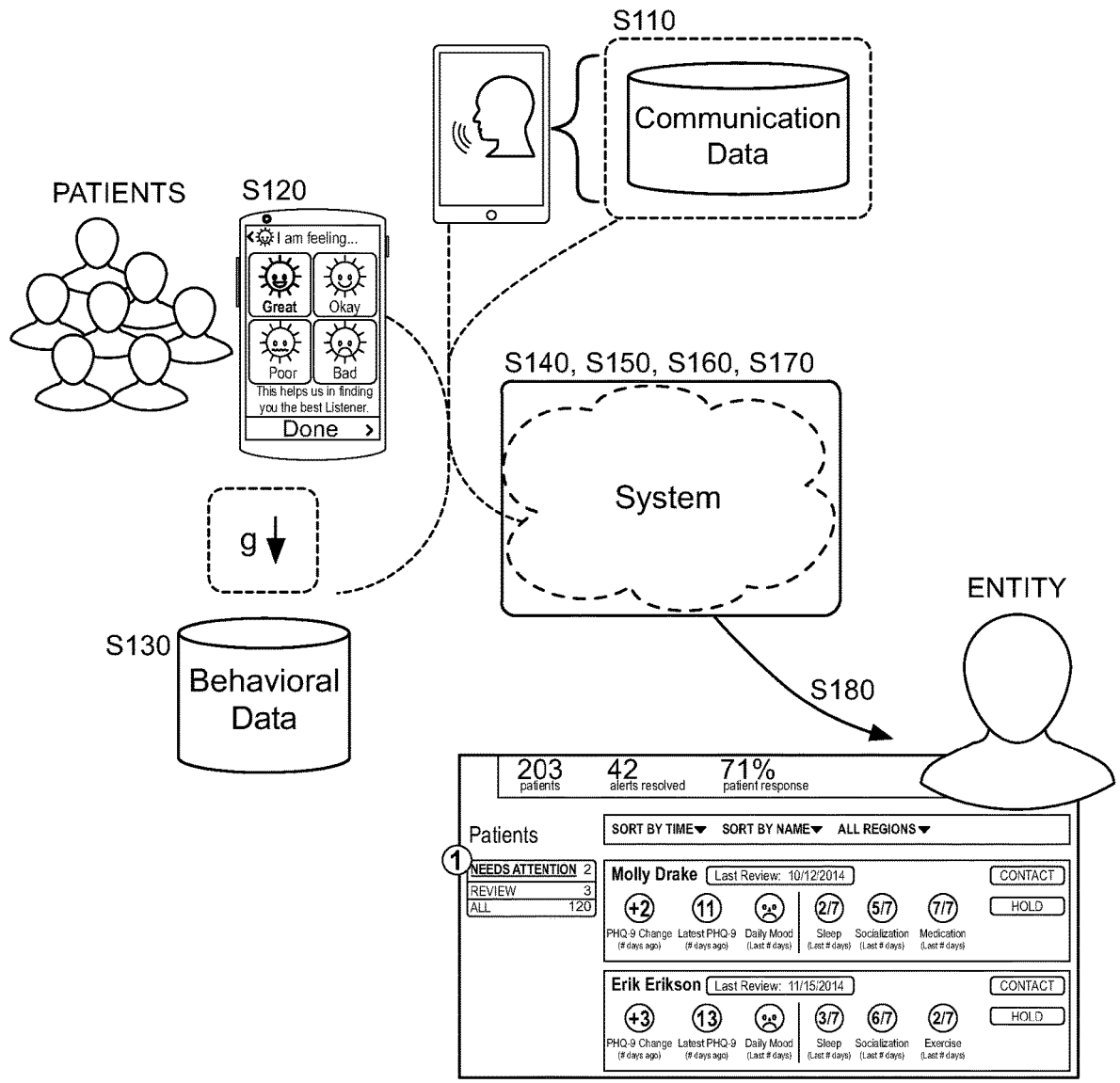
FIG. 1C depict schematics of a variation of a method for providing patient indications to an entity.

The method 100 can be implemented by a processing system in communication with mobile computing devices associated with each of the set of patients, as well as administrative computing systems of the entities prepared to administer interventions (e.g., therapeutic interventions, clinical interventions) to the population of patients in times of need. The processing system can include one or more of: a cloud-based computing platform (e.g., Amazon EC2 or EC3), a mainframe computer system, a grid-computer system, a remote server, and or any other suitable computer system, and can be associated with mobile applications executing on mobile devices of the population of patients, wherein the mobile applications facilitate provision of interventions (e.g., advice, activities) to the population of patients. The method 100 can therefore be implemented using electronic computing devices (e.g., a smartphone, a digital music player, a tablet computer, a wrist-borne mobile computing device, a head-mounted mobile computing device, etc.) executing a native application as shown in FIG. 1C, wherein the electronic computing devices receive inputs derived from behaviors of patients and transmit data derived from the inputs to the processing system, and wherein the processing system generates and provides indications to entities based upon processing of the data. At least one element of the system preferably includes or is coupled to a display such that the method 100 can display information to an entity (e.g., a nurse, anesthesiologist, physician, caretaker, relative, acquaintance, etc.) and/or a patient through the display (e.g., of a mobile computing device), in order to drive interventions (e.g., in-application interventions, therapies, health advice, etc.). Additionally or alternatively, the entity can be a computing system platform (e.g., processing system providing outputs to a dashboard, as described in further detail below), or any other suitable entity. In further detail, the method 100 is preferably implemented at least in part by an embodiment of the system 200 described in Section 2 below; however, the method 100 can alternatively be implemented using any other suitable system configured to process communication and/or other behavior of patients, in aggregation with other information, in order to provide indications to entities prepared to provide interventional help to the patients.

With regard to a population of patients, information derived from the population of patients can be used to provide additional insight into connections between an individual patient's behavior and risk of entering an adverse state (e.g., a critical episode of a condition), due to aggregation of data from the population of patients. The aggregate data can then be used to improve predictive models for providing indications and/or to build improved features into an application executing the method 100. In examples, the population of patients can include individuals characterized or grouped by any suitable demographics, any type of condition for which patients may need help, any type of behavior in interacting with the system(s) implementing the method 100, and/or any other suitable feature.

1.2 Method—Passive Data

Block S110 recites: for each of a population of patients: by way of an application executing at a mobile computing device, accessing a sensor signal processor module and a log of use of a communication application executing on the mobile computing device, which functions to unobtrusively collect and/or retrieve mobility and communication-related data from a patient's mobile computing device. In relation to the sensor signal processing module, Block S110 is preferably implemented using a module of a processing system configured to interface with a sensor signal processing module of a mobile computing device (e.g., smartphone, tablet, personal data assistant (PDA), personal music player, vehicle, head-mounted wearable computing device, wrist-borne wearable computing device, etc.) of a patient, in order to retrieve data that can be used to assess mobility behavior of the patient. In variations, the sensor signal processing module can receive signals derived from one or more of: an accelerometer, a gyroscope, a compass, a GPS module, a force sensor, and any other suitable sensing module that can produce signals indicative of patient mobility. In specific examples, accessing the sensor signal processor module in Block S110 can comprise accessing data derived from one or more of: an Apple M7 chip, an Apple M8 chip, a microprocessor of a mobile computing device, a storage unit of a mobile computing device, and any other specific sensor signal processor module, embodiments, variations, and examples of which are described in U.S. application Ser. No. 15/005,923 filed 25 Jan. 2016. Additionally or alternatively, in Block S110, accessing data indicative of patient mobility can occur by accessing information derived from other native applications (e.g., health monitoring applications, activity monitoring applications, etc.) executing on the mobile device of the patient, for instance, as facilitated using an application programming interface (API). As such, data from the sensor signal processing module can be accessed indirectly through APIs associated with one or more other applications executing on a patient's mobile device. In any of the above embodiments, variations, and examples, accessing a sensor signal processing module can be facilitated using a native application (e.g., a native application with input, output, and data collection functions) installed on the mobile computing device of the patient, and/or in any other suitable manner.

In relation to the log of use of the communication application, Block S110 is preferably implemented using a module of a processing system configured to interface with a native data collection application executing on a mobile computing device (e.g., smartphone, tablet, personal data assistant (PDA), personal music player, vehicle, head-mounted wearable computing device, wrist-borne wearable computing device, etc.) of the patient, in order to retrieve communication-related data pertaining to the patient. As such, in one variation, a native application with data collection functions can be installed on the mobile computing device of the patient (e.g., upon election of installation by the patient, upon promotion of the patient to the individual), can execute substantially continuously while the mobile computing device is in an active state (e.g., in use, in an on-state, in a sleep state, etc.), and can record communication parameters (e.g., communication times, durations, contact entities) of each inbound and/or outbound communication from the mobile computing device. In implementing Block S110, the mobile computing device can then upload this data to a database (e.g., remote server, cloud computing system, storage module), at a desired frequency (e.g., in near real-time, every hour, at the end of each day, etc.) to be accessed by the processing system. In one example of Block S110, the native data collection application can launch on the patient's mobile computing device as a background process that gathers data from the patient once the individual logs into an account, wherein the data includes how and with what frequency the patient interacts with and communicates with other individuals through phone calls, e-mail, instant messaging, an online social network, and/or any other suitable avenue of communication.

As such, in accessing the log of use of the communication application, Block S110 preferably enables collection of one or more of: phone call-related data (e.g., number of sent and/or received calls, call duration, call start and/or end time, location of individual before, during, and/or after a call, and number of and time points of missed or ignored calls); text messaging (e.g., SMS test messaging) data (e.g., number of messages sent and/or received, message length, message entry speed, delay between message completion time point and sending time point, message efficiency, message accuracy, time of sent and/or received messages, location of the individual when receiving and/or sending a message); data on textual messages sent through other communication venues (e.g., public and/or private textual messages sent to contacts of the patient through an online social networking system, reviews of products, services, or businesses through an online ranking and/or review service, status updates, "likes" of content provided through an online social networking system), vocal and textual content (e.g., text and/or voice data that can be used to derive features indicative of negative or positive sentiments) and any other suitable type of data.

In relation to accessing the log of use, Block S110 can include accessing the log of use at the mobile device of the individual, and transmitting, from the mobile device to a computing system, a log of use dataset associated with communication behavior of the individual S112, as shown in FIG. 1B. As such, Block S110 can comprise establishing communication between the computing system and a communication module of the mobile device of the individual, wherein the communication module comprises hardware elements that collect and/or aggregate data associated with communication behavior of the individual. The communication module can thus be accessed (with or without appropriate security aspects) by one or more other portions of the system implementing the method 100, in order to retrieve and process log of use data, according to additional Blocks of the method 100 (described in more detail below). The computing system can be implemented in one or more of a processing module of the mobile device, a personal computer, a remote server, a cloud-based computing system, a computing module of any other suitable computing device (e.g., mobile computing device, wearable computing device, etc.), and any other suitable computing module. In transmitting the log of use dataset, a communication module (e.g., a hardware communication module associated with the communication application) can transmit data to the computing system by way of a wired and/or wireless data link (e.g., a communicable link over Bluetooth, a communicable link over Bluetooth LTE, etc.). However, Block S110 can include another other suitable variation of accessing the log of communication, transmitting data from the log of communication, and/or receiving a log of use dataset.

Similarly, in relation to accessing the sensor signal processor module, Block S110 can include transmitting supplementary data derived from sensor signals, from the mobile communication device S113 and/or any other suitable device (e.g., wearable device, biometric monitoring device, etc.) or system that serves as a source of supplementary data, to the computing system, as shown in FIG. 1B. In transmitting the supplementary dataset, one or more sensor modules (e.g., sensor module of the mobile communication device, sensor module of a wearable computing device, sensor of a biometric monitoring device, etc.) can transmit data to the computing system by way of a wired and/or wireless data link (e.g., over Bluetooth, over Bluetooth LTE, etc.). As such, establishing of a communicable link (e.g., automatically, in response to a triggering condition, manually, etc.) can facilitate transmission of desired data in Block S113. However, Block S113 can include any other suitable variation of transmitting supplementary data, and/or receiving supplementary data 1.3 Method—Survey/Self-Report/Active Data Block S120 recites: using the application, receiving a survey response dataset in association with a time period, which functions to receive active data provided by surveying the patient. Block S120 thus enables generation of active data (e.g., data actively provided by a patient) that can contribute to indication generation in subsequent blocks of the method 100. Block S120 is preferably implemented at a module of the processing system described in relation to Block S110 above, but can additionally or alternatively be implemented at any other suitable system configured to receive survey data from one or more patients. The survey response dataset can include interview and/or self-reported information from the patient. Furthermore, the survey response dataset preferably includes quantitative data, but can additionally or alternatively include qualitative data pertaining to a disorder-related state of the patient and corresponding to a set of time points of the time period. In relation to sensor-derived and communication-derived data received in Block S110, portions of the survey response dataset preferably correspond to a time period overlapping with the time period associated with the sensor-data and communication data; however, portions of the survey response dataset can alternatively correspond to time points outside of the time period associated with Block S110 (e.g., as in a pre-screening or a post-screening survey). Additionally or alternatively, Block S120 can include receiving clinical data (e.g., information gathered in a clinic or laboratory setting by a clinician).

In Block S120, time points of the time period can include uniformly or non-uniformly-spaced time points, and can be constrained within or extend beyond the time period of the log of use of the communication application of Block S110. As such, in variations, the time points of the time period can include regularly-spaced time points (e.g., time points spaced apart by an hour, by a day, by a week, by a month, etc.) with a suitable resolution for enabling detection of changes in a disorder-related state of the patient. Additionally or alternatively, provision of a survey and/or reception of responses to a survey can be triggered upon detection of an event of the patient (e.g., based upon data from sensors associated with the patient, etc.) or any other suitable change in disorder-related state of the patient. Furthermore, the same survey(s) can be provided to the patient for all time points associated with the time period; however, in alternative variations, the same survey(s) may not be provided to the patient for at least one time point associated with the time period.

In variations, the survey response dataset can include responses to one or more surveys configured to assess severity of one or more of: depression, pain, rheumatoid disorders, psychosis (e.g., along a schizophrenia spectrum), cardiovascular disease, sleep disorders, and any other suitable condition or type of condition. Furthermore, the surveys can be configured to transform qualitative information capturing a patient's state into quantitative data according to a response-scoring algorithm. In examples, the survey(s) implemented in Block S120 can be derived from depression-assessment surveys including one or more of: a Hamilton Rating Scale for Depression (HAM-D); the Patient Health Questionnaire (PHQ-9, PHQ-2) for screening, monitoring, and measuring depression severity according to Diagnostic and Statistical Manual (DSM) criteria for depression, which can also give an indication of suicide ideation; the World Health Organization (WHO-5) quality of life assessment; the Patient Activation Measure (PAM) self-management; and any other suitable depression-assessment survey.

Additionally or alternatively, the survey(s) implemented in Block S120 can be derived from pain-assessment surveys including one or more of: a Wong-Baker FACES pain rating scale (with pain rated on a scale from 0-5, 5 being the most severe); a pain visual analog scale (VAS); a pain numeric rating scale (NRS); a verbal pain intensity scale; a brief pain inventory (BPI) tool; a rheumatic disease specific pain scale (DSPI) scored according to sum($X*Y$), where X is the pain level on a 0-10 scale and Y is the percentage of this pain level in a given rheumatic disease group; an Osteoarthritis Research Society International-Outcome Measures in Rheumatoid Arthritis Clinical Trials (OARSI-OMERACT) tool; a survey describing pain location (e.g., with respect to a specific joint, with respect to location within a specific joint); a survey describing pain type (e.g., sharp pain, dull pain, etc.); a survey identifying pain cause (e.g., injury, aging, degeneration, etc.), a survey identifying pain frequency (e.g., with regard to regularity), a survey identifying patterns in pain (e.g., time of pain, weather-related pain, time-of-day-related pain, temperature-related pain, etc.), and any other suitable pain-related survey.

Additionally or alternatively, the survey(s) implemented in Block S120 can be derived from daily functioning and/or activity-assessment surveys including one or more of: a physical activity scale (PAS) survey; a PAS-II survey; a Health Assessment Questionnaire (HAQ, HAQ-II) with scores ranging from 0-3 (with 3 being most severe) a disease activity index (DAI) tool; and any other activity assessment tool. Additionally or alternatively, in examples, the set of symptom-assessment surveys can include surveys focused on symptom exhibition and severity assessment as derived from one or more of: a routine assessment of patient index data tool; a rheumatic arthritis disease activity score (DAS) survey; an arthritis impact measurement scale (AIMS); a British Isles Lupus Assessment Group (BILAG) tool; a systemic lupus erythematosus (SLE) activity questionnaire; an SLE symptom scale survey; and any other suitable survey or tool for assessing symptom exhibition and severity.

Additionally or alternatively, the survey(s) implemented in Block S120 can be derived from psychiatric state assessment surveys including one or more of a Brief Psychiatric Rating Scale (i.e., a 16-18 item survey of psychiatric symptom constructs including somatic concern, anxiety, emotional withdrawal, conceptual disorganization, guilt feelings, tension, mannerisms and posturing, grandiosity, depressive mood, hostility, suspiciousness, hallucinatory behavior, motor retardation, uncooperativeness, unusual thought content, blunted affect, excitement, and disorientation, first published in 1962); a Clinical Global Impression (CGI) rating scale; a Dimensions of Psychosis Symptom Severity scale provided by the American Psychiatric Association; a Global Functioning Role (GFR) survey for phases of Schizophrenia; a Global Functioning Social (GFS) survey for phases of Schizophrenia; a Community Assessment of Psychic Experiences (CAPE) derived survey; a Scale for the Assessment of Positive Symptoms (SAPS) derived survey for delusional behavior, hallucinatory behavior, and/or disorganized speech behavior; and any other suitable tool or survey for assessment of a disorder-related state.

Additionally or alternatively, other survey responses received in Block S120 can include one or more of: a demographic survey that receives demographic information of the patient; a medication adherence survey (for patients taking medication for a psychotic disorder); a mood survey; and a social contact survey (e.g., covering questions regarding aspects of the patient's contact with others). However, the set of surveys can include any other suitable surveys configured to assess mental states of the patient, or adaptations thereof. As such, the survey response dataset can include quantitative scores of the patient for one or more subsets of surveys for each of a set of time points of the time period.

In an example, the survey dataset comprises biweekly responses (e.g., for a period of 6 months) to the PHQ-9 survey, biweekly responses (e.g., for a period of 6 months) to the WHO-5 survey in alternation with the PHQ-9 survey, responses to the PAM assessment at an initial time point, at an intermediate time point (e.g., 1-month time point), and at a termination time point, responses to the HAM-D assessment at an initial time point and a termination time point, biweekly response to a recent care survey, daily responses to a mood survey, and twice-per-week responses to a medication adherence survey.

In some variations, Block S120 can further include facilitating automatic provision of at least one survey at the mobile computing device(s) of the patient(s). As such, responses to one or more surveys can be provided by user input at an electronic device (e.g., a mobile computing device of the patient), or automatically detected from user activity (e.g., using suitable sensors). Additionally or alternatively, provision of at least one survey can be performed manually by an entity associated with a patient or received as derived from clinical data, with data generated from the survey(s) received in Block S120 by manual input. Additionally or alternatively, provision of at least one survey and/or reception of responses to the survey can be guided by way of an application executing at a device (e.g., mobile device, tablet) of a caretaker of the patient and/or the patient, wherein the application provides instruction (e.g., in an audio format, in a graphic format, in a text-based format, etc.) for providing the survey or the responses to the survey. Block S120 can, however, be implemented in any other suitable manner (e.g., by verbal communication over the phone, by verbal communication face-to-face, etc.).

Similar to Block S110, In relation to receiving the survey response dataset, Block S120 can include transmitting the survey response dataset from the mobile communication device S122 and/or any other suitable device or system that serves as a source of survey data, to the computing system, as shown in FIG. 1B. In transmitting the survey dataset, one or more data storage modules (e.g., memory module of the mobile communication device, etc.) can transmit data to the computing system by way of a wired and/or wireless data link (e.g., over Bluetooth, over Bluetooth LTE, etc.). However, Block S120 can include another other suitable variation of transmitting survey data, and/or receiving survey data.

1.4 Method—Generation of Behavioral Dataset

Block S130 recites: generating a behavioral dataset, derived from the sensor signal processor module and the log of use, associated with the time period and derived from passive behavior. Block S130 functions to generate a behavioral dataset based upon unobtrusively collected data from the mobile computing device and/or other device associated with the individual, wherein the device is configured to receive contextual data pertaining to mobility-related behaviors of the individual. The behavioral dataset can thus be subject to clinically-informed behavioral rules (e.g., determined using heuristics), which can contribute to indication generation in subsequent blocks of the method 100. Block S130 can include reception of non-communication-related data pertaining to the individual before, during, and/or after (or in the absence of) communication with another individual (e.g., a phone call) and/or computer network (e.g., an online social networking application), as described above in relation to Block S110. Block S130 can include receiving one or more of: location information, motion information (e.g., related to physical isolation, related to lethargy), device usage information (e.g., screen usage information related to disturbed sleep, restlessness, interest in mobile device activities, usage of mobile device applications, data load attributed to each of a set of mobile device applications), and any other suitable information. The behavioral dataset generated in Block S130 is preferably derived from sensors on-board the mobile computing device (e.g., GPS sensors, accelerometers, gyroscopes, M7 chips, M8 chips) and/or sensors in communication with the mobile computing device (e.g., sensors of devices configured to sync with the mobile computing device), as described in relation to Block S110 above; however, the supplementary dataset can alternatively be derived from any other suitable system.

In variations, Block S130 can include generating location-based behavioral information of the patient by way of one or more of: receiving a GPS location of the patient (e.g., from a GPS sensor on-board the mobile computing device of the individual), estimating the location of the patient through triangulation of local cellular towers in communication with the mobile computing device, identifying a geo-located local Wi-Fi hotspot during a phone call, and any other suitable method for location approximation/identification. In applications, data received in Block S110 and processed in S130 can be used to track behaviors of the patient, such as behaviors indicative of mobility, behaviors indicative of periods of isolation, behaviors indicative of quality of life (e.g., work-life balance based on time spent at specific locations), and any other location-derived behavior information. As such, data from Blocks S110 and S130 can be merged to track the individual's mobility during a communication, in the relation to predictive models and/or analyses generated in subsequent blocks of the method 100. In variations, Block S130 can additionally or alternatively include generating mobile device usage data, including data indicative of screen unlocks and mobile application usage (e.g., by retrieving usage information from mobile operating system logs, by retrieving usage information from a task manager on a mobile computing device, etc.). Blocks S130 and/or S110 can therefore provide data that facilitates tracking of variations and periods of activity/inactivity for a patient through automatically collected data (e.g., from the patient's mobile computing device), in order to enable identification of periods of activity and inactivity of the patient (e.g., periods when the patient was hyperactive on the device or not asleep).

In additional variations, Block S130 can additionally or alternatively include generating one or more of: physical activity- or physical action-related data (e.g., accelerometer and gyroscope data) for the patient, local environmental data (e.g., climate data, temperature data, light parameter data, etc.) associated with the patient, nutrition or diet-related data (e.g., data from food establishment check-ins, data from spectrophotometric analysis, etc.) associated with the patient, biometric data (e.g., data recorded through sensors within the patient's mobile computing device, data recorded through a wearable or other peripheral device in communication with the patient's mobile computing device), and any other suitable data. In examples, one or more of: an activity monitor (e.g., Apple Watch, FitBit device, etc.), a blood pressure sensor, and a pulse-oximeter sensor can transmit the individual's activity behavior, blood pressure, and/or blood oxygen level to a mobile computing device of the patient and/or a processing system implementing portions of the method 100, and Block S130 can include processing this data to further augment models generated in Block S140.

In relation to receiving and processing data, Blocks S130 and/or S110 can additionally or alternatively include receiving data pertaining to individuals in contact with the patient during the period of time, such that data from the patient and data from one or more individuals in communication with the patient are received (e.g., using information from an analogous application executing on the electronic device(s) of the individual(s) in communication with the individual). As such, Blocks S130 and/or S110 can provide a holistic view that aggregates communication behavior data and contextual data of two sides of a communication involving the patient. In examples, such data can include one or more of: an associated individual's location during a phone call with the patient, the associated individual's phone number, the associated individual's length of acquaintance with the patient, and the associated individual's relationship to the patient (e.g., top contact, spouse, family member, friend, coworker, business associate, etc.).

Blocks S120 and S130 can thus provide active data (e.g., self-reported data) and passive data (e.g., unobtrusively collected data) that can be processed in Block S140 to generate predictive models for anticipated disorder-related states of a patient.

1.4.1 Data Structures—Rules

In relation to data acquisition and transmission, rule formats can include: preferences, selections, restrictions, software code, and/or any suitable rule type. Types of rules can include: communication data rules, activity data rules, supplemental data rules, survey data rules, permission rules, and/or any suitable type of rules. Communication data rules, activity data rules, survey data rules, and/or supplemental data rules can include rules relating to time (e.g., when to generate data, when to generate specific types of data, generation in response to which portions of the method 100, etc.), mechanism (e.g., which criteria to base data generation upon, how to analyze raw data in forming processed behavioral data, generating metrics based on comparisons to which baselines, to which users, what kind of data to generate, etc.), location (e.g., which component and/or device sources the behavioral data, etc.), and/or any suitable type of rule. Examples of communication rules include transmitting data over specific communication links (e.g., wireless, wired, etc.), format of responses to requests for data transmission, when to process requests for data transmission, etc. Permission rules can include permission levels for third party accounts (e.g., varying access levels to patient data), user accounts (e.g., varying access levels for users to see a third party's analysis leading to how content is delivered to the user, etc.). However, any suitable type of rule controlling any suitable aspect of the system 200 and/or method 100 can be determined.

Rules can additionally or alternatively be set by a fourth party (e.g., an application programming interface provider, etc.), a third party (e.g., a third party developer, a third party manager of a website and/or application, etc.), a user (e.g., a user of applications associated with the method, etc.), and/or any other suitable entity. Additionally or alternatively, rules can be automatically determined (e.g., rules generated based defined preferences of an individual, rules automatically determined in response to constraints of a user device, etc.). However, any suitable entity can employ any suitable process for generating rules. Rules are preferably customizable with respect to users, third parties, fourth parties, and/or associated accounts, such that different entities can have different permission levels in accordance with the entity's role. For example, a user can be given access to set rules regarding how their behavioral and/or survey data can be viewed on a user device, while a third party developer can be given access to establish a rule for how frequently to request any data from a fourth party database.

1.5 Method—Predictive Model

Block S140 recites: generating a predictive model derived from at least one of the log of use, the survey response dataset, and the behavioral dataset, which functions to provide a predictive model that can generate one or more outputs indicative of an anticipated state of the patient. Generating the predictive model can thus provide supplementary and/or substitutionary information regarding the set of patients, which can be useful when there is limited or no self-reported data (e.g., survey data) from a patient. Preferably, generating the predictive model comprises generating a model that processes features derived from at least one of the log of use, the survey response dataset, and the behavioral dataset and outputs a value of a criticality parameter indicative of a critical state resolvable with intervention. In particular, the predictive model can thus determine a value of a criticality parameter in association with at least one time point (i.e., a time point associated with the time period, a time point outside of the time period based upon extrapolation) in predicting risk that the patient is experiencing a critical symptomatic state, or will trend toward a critical symptomatic state at a future time point. Preferably, generation of the predictive model includes utilization of one or more machine learning techniques and training data (e.g., from the patient, from a population of patients), data mining, and/or statistical approaches to generate more accurate models pertaining to the patient's disorder state (e.g., over time, with aggregation of more data). As such, Block S140 is preferably implemented at a processing system configured to process data from the log of use, the survey response dataset, and the behavioral dataset; however, the predictive model generated in Block S140 can alternatively be implemented in any other suitable manner.

1.5.1 Predictive Model—Features and Triggers

In generating the predictive model, Block S140 preferably uses input data including communication behavior data from the log of use, data from the survey response dataset, and data from the behavioral dataset to provide a set of features and/or feature vectors corresponding to time points of the time period. The features can be behavioral features, and can function as predictive variables for the predictive model. Furthermore, one or more of the features can be quantitative and one or more of the behavioral features can be qualitative. Furthermore, the features can include raw computed values from outputs of other blocks of the method 100, and/or can be normalized (e.g., normalized to norms for an individual or a group of individuals).

In a specific example, Block S140 can include generating behavioral features from one or more outputs of the previously described blocks of the method 100, including one or more of: a communication volume feature that captures an amount of communication (e.g., via calling, via texting) by a patient; a communication diversity feature that captures a diversity (e.g., in terms of variety of people communicated with, in terms of variety of time points associated with communication, etc.) in communications involving a patient; a communication predictability feature that captures predictability and unpredictability of communications involving a patient; a communication entropy feature that captures an extent to which communication behavior of a patient is trending toward disorder; a mobility feature that captures an amount of mobility-related activity of a patient; a mobility radius feature that captures a distance moved by a patient; and an active time by category feature that categorically describes activities of a patient. Features can be broken down by time (e.g., in association with peak times, in association with non-peak times, in association with working hours, in association with non-working hours, in association with weekend days, in association with weekday days, in association with mornings, in association with afternoons, in association with evenings, in association with late nights, in association with other time periods, etc.). Features can additionally or alternatively be aggregated over various times windows (e.g., on the order of sub-seconds, on the order of seconds, on the order of minutes, on the order of hours, on the order of days, on the order of weeks, on the order of months, etc.). Variations of the specific example can, however, include any other behavioral features, organized in any other suitable manner in relation to time, and aggregated over any other suitable time window.

In relation to the features described above, Block S140 can include abstraction of features into a class of features, wherein abstraction functions to create features that are in a form that is more interpretable by humans (or other non-computing entities). The abstracted features can function as triggers for provision of interventions to one or more patients according to the method 100, in the form of outreach by an entity (e.g., listening entity, coaching entity, therapeutic entity, etc.), health advice, activities presented in a mobile application environment intended to be performed by a patient, and any other suitable intervention.

In a specific example, Block S140 can include generating trigger features from one or more outputs of the previously described blocks of the method 100, including one or more of: a physical isolation feature (e.g., derived from processing of GPS data); a social isolation feature (e.g., derived from processing of log of use data); a sleep quality feature (e.g., derived from processing of mobile device usage data, activity data, and time stamped data); a feature associated with restlessness (e.g., derived from mobile device usage data, time stamped data); a feature associated with feelings of being overwhelmed (e.g., derived from GPS data and time stamped data); a feature associated with lethargy (e.g., derived from GPS data and activity data); a feature associated with support outreach (e.g., receiving communication from or reaching out to supporting entities); a feature associated with feelings of being overstimulation (e.g., derived from log of use data, mobile device usage data, and activity data); a feature associated with boredom (e.g., derived from mobile device usage data, GPS data, and time stamped data); a feature associated with aberrant behavior (e.g., derived from mobile device usage data, log of use data, and activity data); and any other suitable feature. In the specific example, creation of trigger features can include abstracting and deriving such features from a combination of different behavioral data components associated or otherwise mapped to interpretable symptoms/outcomes pertaining to a patient; however, creation of features can be performed in any other suitable manner. Furthermore, while trigger features can be used in an automated manner to automatically providing interventions to an individual, trigger features can alternatively be delivered to a human entity (e.g., coaching entity, listening entity, therapeutic entity, etc.) for additional processing, prior to intervention provision, as described further below in relation to reports, dashboards, and tools. For instance, use of trigger features can benefit from some processing by a trained entity who is in direct contact with a patient exhibiting the trigger feature(s).

In more detail, some feature generation or feature selection approaches can include one or more of: factor analysis approaches that implement statistical methods to describe variability among observed features in terms of unobserved factors, in order to determine which features explain a high percentage of variation in data; correlation feature selection (CFS) methods, consistency methods, relief methods, information gain methods, symmetrical uncertainty methods, and any other suitable methods of feature selection. In variations, feature selection approaches can be implemented for any passive data (e.g., communication data, mobility data), wherein a linking analysis of Block S140 is then used to determine associations between features of passive data and states of disorder determined from active data (e.g., survey response datasets). Analysis of the passive data in relation to the active data, with regard to feature selection and associations between passive and active data can, however, be performed in any other suitable manner.

In one variation, the feature vectors can include features related to aggregate communication behavior, interaction diversity, mobility behavior (e.g., mobility radius), a number of missed calls, and a duration of time spent in a certain location (e.g., at home). In examples, feature vectors can be generated based upon aggregation of phone, text message, email, social networking, and/or other patient communication data for a particular period of time into one or more features for the patient for the particular time period. Furthermore, a feature can be specific to a day, a week, a month, a day period (e.g., morning, afternoon, evening, night), a time block during a day (e.g., one hour), a specific communication action (e.g., a single phone call, a set of communication actions of the same type (e.g., a set of phone calls within a two-hour period), all communications within a period of time, etc.). Additionally, combinations of features can be used in a feature vector. For example, one feature can include a weighted composite of the frequency, duration (i.e., length), timing (i.e., start and/or termination), and contact diversity of all outgoing voice (e.g., phone call) communications and a frequency, length, and timing and/or response time to (i.e., time to accept) incoming voice communications within the first period of time through a phone call application executing on the patient's mobile computing device. Feature vectors can additionally or alternatively include features based on analysis of voice communications, textual communications, mobile application activity usage, location data, and any other suitable data which can be based on variance, entropy, or other mathematical and probabilistic computations of basic data (e.g., a composite activity score, a composite socialization score, a work-life balance score, a quality-of-life score). However, the feature vectors can be determined in any other suitable manner.

In some variations, Block S140 can utilize statistics-based feature selection approaches to determine a subset of features from the log of use, the survey dataset, and/or the supplementary dataset that have a high predictive power and/or high accuracy in generating the value(s) of a criticality parameter as an output of the predictive model. Furthermore, the statistical approaches can be used to strategically reduce portions of data collected based upon redundancy and/or lack of utility of the data. Even further, the statistical approaches/feature selection approaches can be used to entirely omit collection of portions of the data (e.g., responses to specific surveys or portions of surveys can render responses to other portions of surveys or other surveys redundant), in order to streamline the data collection in Blocks S110, S120, and/or S130. In examples, the statistical approaches can implement one or more of: correlation-based feature selection (CFS), minimum redundancy maximum relevance (mRMR), Relief-F, symmetrical uncertainty, information gain, decision tree analysis (alternating decision tree analysis, best-first decision tree analysis, decision stump tree analysis, functional tree analysis, C4.5 decision tree analysis, repeated incremental pruning analysis, logistic alternating decision tree analysis, logistic model tree analysis, nearest neighbor generalized exemplar analysis, association analysis, divide-and-conquer analysis, random tree analysis, decision-regression tree analysis with reduced error pruning, ripple down rule analysis, classification and regression tree analysis) to reduce questions from provided surveys to a subset of effective questions, and other statistical methods and statistic fitting techniques to select a subset of features having high efficacy from the data collected in Blocks S110, S120, and/or S130. Additionally or alternatively, any assessment of redundancy or efficacy in a feature derived from data of Blocks S110, S120, and/or S130 can be used to provide a measure of confidence in a symptom criticality parameter produced by the predictive model from one or more input features.

In some embodiments, the predictive model generated in Block S140 can process a set of feature vectors according to methods described in relation to the predictive modeling engine described in U.S. application Ser. No. 13/969,339, entitled "Method for Modeling Behavior and Health Changes" and filed on 16 Aug. 2014, which is incorporated herein in its entirety by this reference; however, the predictive model can alternatively be generated in any other suitable manner. As such, in variations of the model(s), a set of feature vectors from the input data can be processed according to a machine learning technique (e.g., support vector machine with a training dataset) to generate the value(s) of the criticality parameter in association with a time point. In one example, the predictive model can incorporate historical data from the patient (e.g., survey responses from a prior week, a history of passive data from the log of use, etc.), with more weight placed upon more recent data from Blocks S110-S130 in generation of the criticality parameter by the predictive model; however, the predictive model can be implemented in any other suitable manner.

While some variations of machine learning techniques are described above, in relation to generation of the predictive model, Block S140 can additionally or alternatively utilize any other suitable machine learning algorithms. In variations, the machine learning algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

1.6 Method—Analyses and Conditions for Interventions

Block S150 recites: generating a first comparison between the survey response dataset and a first threshold condition, a second comparison between the behavioral dataset and a second threshold condition, and a third comparison between an output of the predictive model and a third threshold condition. Block S150 functions to process the outputs of Blocks S110-S140 of the method 100, such that the indication generated in Block S160 for a patient has at least one of an active component (i.e., a component derived from the survey response dataset), a behavioral component (e.g., a clinically-informed behavioral rule component determined by heuristics), and a component derived from the predictive model generated in Block S140. Block S150 can include generating comparisons in relation to threshold conditions of varying levels of conservativeness and/or having primary and secondary components, depending upon characteristics of the patient and/or other factors (e.g., different use cases of a mobile application associated with the method). Furthermore, the comparisons generated in Block S150 can be used as triggers to improve patient engagement in the short term, and/or patient health outcomes in the long term. Additionally or alternatively, the comparisons can be used to inform decisions implemented within software and/or implemented by an entity associated with a patient, to provide relevant interventions (e.g., stress-relaxation interventions, cognitive behavioral therapy-based interventions, etc.) to a patient.

Preferably, triggers derived from the comparisons of Block S150 are non-real-time triggers that enable identification of persistence in symptoms (e.g., persistence in symptoms over the course of a few days, over the course of a week, etc.); however, triggers derived from the comparisons of Block S150 can alternatively be near-real-time triggers that enable near-immediate responses to a non-persistent state of a patient. In relation to other blocks of the method 100 associated with accounting for limited resource use and/or promoting patient engagement without being overbearing, any triggers generated can have an associated quota. For instance, each patient associated with an entity can have one allotted trigger per week, if the patient has not received any other interventions within the week. However, the number of triggers generated for each of a population of patients can alternatively not have an associated quota.

Figure 2:
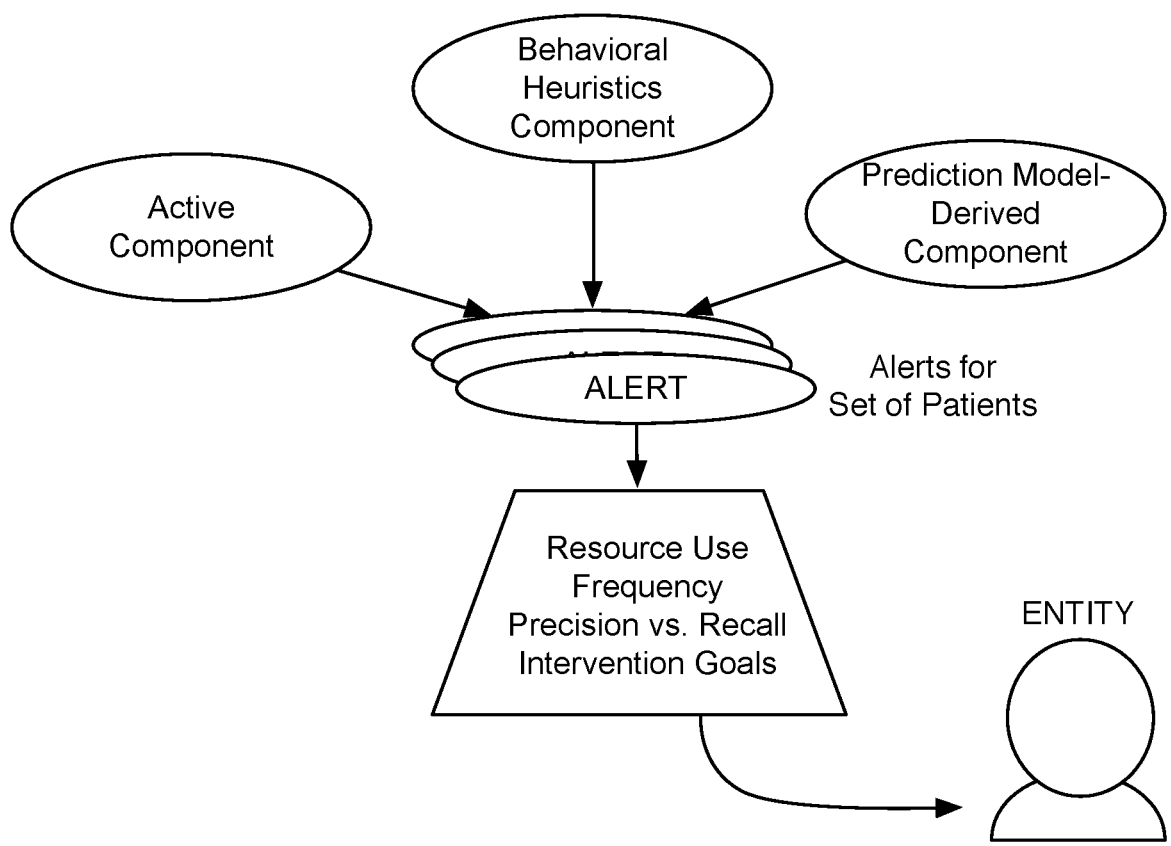
FIG. 2 depicts a variation of a method for providing patient indications to an entity.

In particular, in Block S150, consideration of the active component, the behavioral component, and the component derived from the predictive model can significantly strengthen the efficacy of the indication generated for a patient in Block S160, as shown in FIG. 2. Furthermore, each of the active component, the behavioral component, and the predictive model component can have an associated time frame that is identical or different to time frames of analysis of the other components. Additionally, analysis of each of the active component, the behavioral component, and the predictive model component can occur within one or more time frames that are different from the time frame of indication provision in Blocks S170 and S180. In view of the population of patients, consideration of the active component, the behavioral component, and the component derived from the predictive model facilitates prioritization of indications generated for different patients, given, for instance, resource constraints in providing suitable interventions for patients in need.

In Block S150, generating the first comparison between the survey response dataset and a first threshold condition can comprise assigning a score to a survey response dataset for a patient (e.g., based upon one instance of survey response provision, based upon multiple instances of survey response provision), and comparing the score to the first threshold condition. In variations wherein the survey response dataset comprises responses to survey questions (e.g., a repeat set of survey questions) at each of a set of time points, the first threshold condition can additionally or alternatively include a frequency threshold and/or a frequency-within-a-duration-of-time threshold, in relation to generation of an indication based upon an active component. Furthermore, threshold conditions can be defined in relation to a baseline for each patient, based upon historical behavior of the patient. As such, in variations, a comparison can indicate one or more of: a score greater than a given threshold; a score greater than a given threshold for a certain duration of time; a change in score greater than a given threshold; a change in score greater than a given threshold as derived from the patient's historical score data; and any other suitable comparison. Furthermore, the comparison(s) can additionally or alternatively be generated based upon a percentile condition, a standard deviation (e.g., in score) condition, outlier detection analysis (e.g., of a score in relation to scores from the user), and/or any other suitable condition, based upon analysis of a patient in isolation, based upon analysis of the patient's recent behavior in isolation, based upon analysis of a population of patients, and/or any other suitable grouping of patients.

Additionally or alternatively, the comparison(s) generated in Block S150 can include identification or analysis of patient progress through a condition (e.g., in relation to persistence of symptoms, in relation to worsening of symptoms, in relation to improvement of symptoms, etc.).

In examples, the comparison can facilitate identification of one or more of: a score for survey responses that surpasses a critical threshold score (e.g., a score above a critical value on a PHQ-9 survey, a score above a threshold value on an individual item of a survey, etc.); a change in survey score that surpasses a critical threshold; a set of scores for survey responses acquired at each of a set of time points within a duration of time, wherein a threshold proportion of the set of scores surpasses a critical threshold score (e.g., 2 of 3 surveys have scores above a critical threshold); a summation of scores for a set of scores for survey responses acquired at each of a set of time points that surpasses a critical threshold; a magnitude of difference in scores for survey responses acquired at different time points that surpasses a critical threshold (e.g., a PHQ-9 score >15, which is greater than a previous score); a combination of scores for different surveys that surpasses a critical threshold for each of the different surveys; and any other suitable condition for indication generation.

In specific example, the first comparison can include a comparison between PHQ-9 scores and different thresholds of varying levels of conservativeness. The PHQ-9 scores can be collected at a first frequency, wherein the first frequency is a biweekly frequency; however, PHQ-9 scores can alternatively be collected at any other suitable frequency (e.g., daily, weekly, biweekly, monthly, etc.). In more detail, the first comparison can be associated with a primary threshold condition of a mean of two consecutively scheduled PHQ-9 scores that are greater than or equal to 15 and with a difference greater than zero. The first comparison can be associated with a secondary threshold condition of three consecutively scheduled PHQ-9 scores that are greater than 15, which covers situations wherein the trend in PHQ-9 scores is downwards but the patient still has a PHQ-9 score above 15. In the example, the first comparison can additionally or alternatively include a condition that enables determination of exhibition of suicide ideation by the patient (e.g., a threshold condition of a score above zero on a question of the PHQ-9 related to suicide ideation).

Additionally or alternatively, in a second specific example, the first comparison can include a comparison between PHQ-2 scores and different thresholds of varying levels of conservativeness. The PHQ-2 scores can be collected at a second frequency, wherein the second frequency is different from a first frequency for PHQ-9 score collection (e.g., a daily frequency for monitoring of daily fluctuations in state); however, PHQ-2 scores can alternatively be collected at any other suitable frequency (e.g., daily, weekly, biweekly, monthly, etc.). In more detail, the first comparison can be associated with a more conservative threshold condition of an average PHQ-2 score greater than the 90th percentile of scores (e.g., for a window of 14 days and with a minimum of 10 scores), for 3 consecutive days. Under this threshold condition, a maximum of one alert should be generated within a certain duration of time (e.g., one alert within 5 days, according to resource constraints, etc.). In this example, the first comparison can additionally or alternatively be associated with a less conservative threshold condition of an average PHQ-2 score greater than the 80th percentile of scores (e.g., for a window of 14 days and with a minimum of 10 scores), for 3 consecutive days. Under this threshold condition, a maximum of one alert should be generated within a certain duration of time (e.g., one alert within 5 days, according to resource constraints, etc.). In more detail, any limits on alert generation/provision to an entity can be implemented in order to promote one or more of: efficient use of constrained resources (e.g., time of an entity, financial resources, etc.), meaningful interactions between an intervening entity and a user, positive relationships (e.g., non-intrusive) relationships between an intervening entity and a user, and any other suitable factor.

Additionally or alternatively, in a third specific example, the first comparison can be made with respect to a threshold condition associated with persistent and/or worsening depression symptoms, as exhibited by scores above threshold scores for questions related to sleep, appetite, and/or concentration on a PHQ-9 survey, wherein the scores have changed above a threshold amount relative to previous scores. Additionally or alternatively, in a related variation of this specific example, the first comparison can be made with respect to a threshold condition associated with persistent and/or worsening depression symptoms, as exhibited by scores above threshold scores for questions on a PHQ-2 survey, wherein the scores have changed above a threshold amount relative to previous scores. Additionally or alternatively, in a related variation of this specific example, the first comparison can be made with respect to a threshold condition associated with persistent and/or worsening anxiety symptoms, as exhibited by scores above threshold scores for questions on a GAD-7 survey, wherein the scores have changed above a threshold amount relative to previous scores. Additionally or alternatively, in a related variation of this specific example, the first comparison can be made with respect to a threshold condition associated with persistent and/or worsening anxiety symptoms, as exhibited by scores above threshold scores for questions on an anxiety survey provided to the patient daily, wherein the scores have changed above a threshold amount relative to previous scores.

In Block S150, generating the second comparison between the behavioral dataset and a second threshold condition can comprise defining one or more passive behavior (e.g., related to lethargy, related to social isolation, related to physical isolation, related to evolution of the patient's support network, related to time spent at work, related to weekly behavioral patterns, related to disturbed sleep behavior, related to normal sleep behavior, etc.) based upon historical behavior of a patient within a duration of time (e.g., immediately prior 4-6 weeks of the patient's life). Then, the features of or evolution in the passive heuristic(s) for the patient can be compared to the second threshold condition. In variations wherein the passive behavior for the patient are monitored for a duration of time, the second threshold condition can additionally or alternatively include a frequency threshold and/or a frequency-within-a-duration-of-time threshold, in relation to generation of an indication based upon a behavioral component. In examples, the comparison can facilitate identification of one or more of: a period of lethargy exhibited as a persistent reduction in mobility (e.g., mobility behavior lower than $20^{th}$ percentile or $25^{th}$ percentile over a period of 3 consecutive days); a period of social isolation exhibited as persistence in unreturned communications (e.g., a period of 3 days of unreturned phone calls, a period of 3 days of unreturned text-based communications, a number of instances of unreturned calls, a number of unreturned text-based communications, etc.); a period of physical isolation exhibited as persistence in staying in a location (e.g., staying primarily at the same location over a threshold duration of time per day, for a period of 3 or more days); a reduction in the patient's support network exhibited as communicating with fewer people than typical for the patient (e.g., a communication count in the top $15^{th}$ percentile or $20^{th}$ percentile, and a communication diversity below the $40^{th}$ percentile, for a duration of time); a combination of multiple passive behaviors that satisfy a threshold condition (e.g., two passive behavior that meet a threshold within 3 days); and any other suitable condition for indication generation.

In an additional specific example, generating a second comparison can facilitate identification of a period of restlessness exhibited as abnormal mobile device usage by the patient within a certain duration of time. In relation to this example, Block S150 can include one or more of: comparing a number of screen interactions between the patient and his/her mobile device in a short time window to a threshold number of screen interactions, thereby enabling identification of impulsivity in mobile device usage; and comparing a number of instances of switching between mobile applications executing on the mobile device within a short time window to a threshold number of switches (e.g., 3 switches within 48 hours, a number of switches within a certain percentile of switches for a 2 hour window of time, etc.). In this specific example, the second comparison can thus be used to govern provision of a stress-reduction intervention (e.g., calming exercises provided by way of a mobile device application) to the patient.

In an additional specific example, generating a second comparison can facilitate identification of a period of busyness or exhaustion of the patient, exhibited as an extensive amount of time spent at work within a certain duration of time. In relation to this example, Block S150 can include one or more of: comparing an amount of time spent at work to a threshold condition (e.g., 2 hours greater than a trailing average where the threshold has been crossed a certain number of times within a period of time). In this specific example, the second comparison can thus be used to govern provision of a stress-reduction intervention (e.g., calming exercises provided by way of a mobile device application) to the patient.

In an additional specific example, generating a second comparison can facilitate identification of a period of hyperactivity of the patient, exhibited as an increase in physical activity and communication behavior within a certain duration of time. In relation to this example, Block S150 can include one or more of: comparing an aggregated communication parameter (e.g., associated with phone calling behavior, associated with text messaging behavior, etc.) to a threshold condition (e.g., associated with duration of communications, number of communications, etc.); and comparing a physical activity parameter (determined from mobility data) to a threshold condition (e.g., associated with average duration of physical activity over time, etc.). In this specific example, the second comparison can thus be used to govern provision of a stress-reduction intervention (e.g., calming exercises provided by way of a mobile device application) to the patient.

In an additional specific example, generating a second comparison can facilitate identification of a period of poor sleep behavior of the patient, exhibited as an inability to fall asleep at a regular hour and/or an inability to get a certain amount of sleep for a certain duration of time. In relation to this example, Block S150 can include one or more of: comparing an average bedtime calculated over a duration of time to a threshold bedtime; and comparing an average amount of sleep calculated over a duration of time to a threshold amount of sleep. In this specific example, the second comparison can thus be used to govern provision of a stress-reduction intervention (e.g., calming exercises provided by way of a mobile device application) to the patient.

In an additional specific example, generating a second comparison can facilitate identification of a period of social and physical isolation of the patient, exhibited as an increase in the amount of time spent in isolation (e.g., at home), and/or a decrease in aggregate communication. In relation to this example, Block S150 can include one or more of: comparing an average duration of time spent at home over a window of time to a threshold duration; and comparing an aggregated communication parameter related to an amount of communication by the patient, to a threshold amount. In this specific example, the second comparison can thus be used to govern provision of a stress-reduction intervention (e.g., calming exercises provided by way of a mobile device application, exercises for mitigating negative thought processes provided by way of a mobile device application) to the patient.

In an additional specific example, generating a second comparison can facilitate identification of a period of boredom of the patient, exhibited as an increase in behaviors indicative of under-stimulation. In relation to this example, Block S150 can include one or more of: comparing an average duration of time within which the patient maintains a certain mobile device screen configuration to a threshold duration of time; and comparing a mobility radius of the patient to a threshold mobility radius, for the duration of time in which the patient maintains the mobile device screen configuration. In this specific example, the second comparison can thus be used to govern provision of a stress-reduction intervention (e.g., calming exercises provided by way of a mobile device application) to the patient.

In an additional specific example, generating a second comparison can facilitate identification of a period of irregular behavior of the patient, exhibited as an increase in behaviors indicative of lack of focus, distraction, and/or irregular communications. In relation to this example, Block S150 can include one or more of: comparing a change in one or more behavioral features described above to a threshold change condition; comparing a change in a value of an off-peak time (e.g., evening) communication behavior parameter to a threshold value; and comparing any other suitable change in behavior to a threshold change. In this specific example, the second comparison can thus be used to govern provision of a stress-reduction intervention (e.g., calming exercises provided by way of a mobile device application) to the patient.

In Block S150, generating the third comparison between the output of the predictive model and a third threshold condition can comprise identification of a classification (e.g., a learned, complex, non-intuitive, and/or behavioral association exhibited by the patient), and comparing the classification to a threshold condition. In variations, a single feature and/or combinations of features derived from the log of use, the survey response dataset, and the behavioral dataset (e.g., with weighting among factors) can be compared to one or more threshold conditions, in identifying if an indication based upon the predictive model of Block S140 should be generated. In variations and examples, the third comparison can be generated as described in U.S. application Ser. No. 13/969,339, entitled "Method for Modeling Behavior and Health Changes" and filed on 16 Aug. 2014.

As such, in one example of Block S150, accounting for an active component, a behavioral component, and a predictive model component, an indication can be based upon: scoring of a biweekly survey, a first passive behavioral component generated from a first 3-day window of time, a second passive behavioral component generated from a second window of time overlapping with the first 3-day window of time, and a predictive model component for a time window of 14 days (e.g., overlapping with the period of the biweekly survey), wherein the predictive model component implements an aggregated learning approach based upon multiple individual models (e.g., each assessing different parameters and/or different time periods of patient behavior).

1.7 Method—Patient Population Handling

Block S160 recites: generating an indication in response to at least one of the first, the second, and the third comparisons, thereby producing a set of indications corresponding to a subset of patients of the set of patients. Block S160 functions to transform the comparisons generated in Block S150 into an indication pertaining to a condition of the patient. The indication can be generated based upon an active component (e.g., survey response-derived indication), a behavioral component (e.g., a behavioral heuristics-derived indication), or a predictive model derived component. However, the indication can additionally or alternatively be generated based upon a combination of two or more of the active component, the behavioral component, and the predictive model-derived component, or two or more constituents of each of the active component, the behavioral component, and the predictive model-derived component. In generating an indication based upon one of the active component, the behavioral component, and the predictive model-derived component, the indication can be generated based upon satisfaction of a threshold condition. In one example, an indication can be generated if survey scores satisfy the first threshold condition in two of three previous surveys, associated with a time period of the immediately prior 7 days. In another example, an indication can be generated if two passive behaviors satisfy a second threshold condition within a duration of three days.

As noted above, in some variations, indications derived from two or more of the active component, the behavioral component, and the predictive model derived component can be combined in generation of the indication. In one variation, satisfaction or dissatisfaction of a threshold condition for an active component, in combination with satisfaction or dissatisfaction of a threshold condition for a behavior component and/or a predictive model-derived component can result in generation of the indication. Additionally or alternatively, in another variation, each of the first comparison, the second comparison, and the third comparison of Block S150 can have an associated weight, wherein the associated weight contributes higher consideration or lower consideration of the component in generation of the indication. In one specific example, an active component (e.g., survey response derived component) can be weighted more heavily than a behavioral component and/or a predictive model-derived component, in generation of the indication of Block S160. Additionally or alternatively, in another variation, at least one component (e.g., active, behavioral, predictive model-derived) can have a "trump card" condition, wherein if the trump card condition is satisfied, an indication is generated regardless of the other components. In one specific example, a PHQ-9 score >15 can result in generation of an indication, regardless of behavioral and predictive model derived considerations. Combination of different components in generation of the indication can, however, be performed in any other suitable manner.

In generating the indication for a patient, the indication can be classified according to one of a set of levels. In one variation, the indication can be classified as belonging to one of a first level and a second level. In this variation, the first level of indication pertains to indications with interventions that require a high level of resource use, and/or interventions that put a high level of burden on the patient. In an example, the first level of indication can contribute to a requirement for a coaching entity, a therapist, a nurse, and/or a physician outreach to the patient (i.e., a high level of resource use), and can contribute to a session of cognitive behavioral therapy (CBT). Furthermore, in this variation, the second level of indication pertains to indications with interventions that require a low level of resource use, and/or interventions that put a low level of burden on the patient. In an example, the second level of indication can contribute to provision of a health-tip (e.g., automatically generated advice provided by way of an electronic device of the patient), and can additionally or alternatively contribute to a session of CBT. Block S160 can, however, include any other suitable alternative variation of indication classification.

In any of the above variations and examples of Block S160, a frequency of indication provision can be constrained (e.g., so as to not overburden an entity prepared to intervene in improving a patient's condition). In examples, a maximum of one indication within a seven day window, per patient, can serve as a limiting frequency of indication provision to the entity.

Furthermore, generating the indication in Block S160 can include identifying an appropriate intervention category based on the indication (e.g., a specific type of indication can be used as a filter for identifying a subset of appropriate interventions to deliver to the user). In more detail, intervention categories can be identified, and observed behaviors of the individual can be associated with specific intervention categories, such that an indication based on an observed behavior can be used to trigger provision of a specific intervention of the appropriate category.

In a specific example, exhibition of restless behavior (e.g., as determined from an increase in mobile device screen interactions, as determined from a change in the mean/variance of inter-event times between mobile device screen pairs of "on" events and "off events) can be used to promote mindfulness activities (e.g., breathing activities) to the patient. In another specific example, exhibition of restless behavior (e.g., as determined from detection of pacing of the patient from activity monitoring sensors of the patient) can be used to promote mindfulness activities (e.g., breathing activities) to the patient. In another specific example, identification of an increase in time spent at work by a patient (e.g., from GPS data of the patient) can be used to promote interventions associated with increasing "savoring" of life to the patient. In another specific example, identification of a decrease in time spent at work by a patient (e.g., from GPS data of the patient) can be used to promote interventions associated with increasing focus to the patient. In another specific example, identification of an increase in busy-ness of a patient (e.g., from a detected increase in mobility, from a detected increase in communication, etc.) can be used to promote mindfulness activities to the patient. In another specific example, detection of a decrease in focus of a patient (e.g., from detected increases in switching between different mobile device applications, different content sources, etc.) can be used to promote mindfulness activities to the patient. In another specific example, detection of changes in sleep behavior (e.g., a decrease in sleep amount, an increase in sleep amount, abnormal interruptions of sleep, change in regularity of sleep and awake times, etc.) of a patient can be used to promote sleep-improving interventions to the patient. In another specific example, detection of social and/or physical isolation behaviors of the individual can be used to promote interventions to the patient that reduce isolation of the patient. In another specific example, detection of lethargy of the patient (e.g., from a reduction in mobility radius, etc.) can be used to promote focus-oriented interventions or physical activity increasing interventions to the patient. Furthermore, in relation to any changes in behavior of a patient, the behaviors can be monitored for a period of time to assess if the changes are beneficial or detrimental, before providing interventions that correct or reinforce such behaviors.

However, indications and categories of interventions can additionally or alternatively be associated or used in any other suitable manner.

Block S170 recites: ranking the set of indications according to a severity factor, which functions to organize the set of indications, in prioritizing patients requiring more immediate attention. Block S170 functions to assess urgency of the condition of each patient, in order to effectively prioritize patients who are characterized by a more severe state than other patients. In Block S170, and as shown in FIG. 2, the severity factor according to which each of the set of indications is ranked can be based upon one or more of: patient state (e.g., an acute state, a medicated state, a state of remission, etc.); resource use (e.g., the intervention action driven by the indication, the amount of burden put upon patients to receive an intervention, financial costs of intervention, etc.); goals of an intervention resulting from the indication for a patient (e.g., a goal of intervening while the patient is experiencing an episode, a goal of intervening prior to experiencing of an episode by the patient, a goal of preventing a certain patient condition, a goal of treating a certain patient condition, etc.); a desired frequency of indication provision pertaining to a given patient (e.g., in relation to specifics of a condition, in relation to how an episode or flare is defined for a condition, in relation to duration of time that has passed since an indication pertaining to a patient was transmitted to the entity, etc.); a consideration of indication precision (e.g., high precision and efficient resource use); a consideration of patient recall (e.g., lower precision and less efficient resource use); and any other suitable factor. In relation to the variation described above, wherein the indication is classified according to one of a first indication level and a second indication level, the first indication level can be associated with a high value of the severity factor, and the second indication level can be associated with a low value of the severity factor. However, ranking the set of indications for the population of patients can alternatively be performed in any other suitable manner and/or based upon any other suitable considerations.

Additionally or alternatively, Block S170 can include organizing the set of indications based upon one or more of: a most recent time point associated with outreach/intervention for a patient (e.g., in relation to a previous in-person visit, in relation to a previous phone call intervention, etc.); medication adherence of a patient, resiliency factors (e.g., self-reported or non-self reported indications that a patient is capable of managing their condition, despite severity of the condition); user non-adherence to meeting goals (e.g., health-related goals set by their caretaker); and any other suitable factor. Furthermore, Block S170 can include ranking, organizing, or otherwise prioritizing groups of patients according to one or more of the discussed factors. Additionally, consideration of indications for transmission to the entity can be based upon patient-population and workflow related constraints including one or more of: number of indications generated (e.g., for a patient, for a patient population) in a given time period (e.g., one week, one month); a duration of time between adjacent indications (e.g., for a patient); and any other suitable factor.

Block S180 recites: transmitting a portion of the set of indications to the entity according to a resource constraint of the entity, which functions to provide indications to the entity(ies) associated with the population of patients, in a manner that considers constraints of the entity(ies). In Block S180, the resource constraint can be determined based upon experience, for instance, by transmitting a test number and/or frequency of indications (e.g., indications with different classification levels, indications with identical classification levels) to the entity, and receiving feedback from the entity regarding appropriateness of the test number of indications. Then, in future instances, the number and/or frequency of indications can be modulated according to feedback from the entity. Additionally or alternatively, the appropriate number/frequency of indications transmitted to an entity can be predetermined, for instance, by accessing a calendar of workflow for the entity. Determination of the appropriate number/frequency of indications transmitted to an entity can, however, be performed in any other suitable manner.

In Block S180, a transmitted indication can comprise one or more of a visual indication (e.g., text-based indication, graphic indication), audio indication, haptic indication, and/or any other suitable type of indication. In relation to an entity associated with the patient(s), the entity can include any one or more of: a healthcare provider (e.g., nurse, physician), a caretaker, a relative (e.g., parent, significant other, etc.), and any other suitable entity associated with the patient. Furthermore, in relation to an entity associated with the patient(s), the indication(s) can be provided at a dashboard of an electronic interface (e.g., web portal, computing device, etc.) accessible by the entity.

In some variations, a transmitted indication may also be hidden and/or configured to trigger other features within a platform for intervention provision to one or more patients. For instance, an indication generated based on outputs of previous blocks of the method 100 can be used to trigger provision of an intervention (e.g., an intervention in the form of health advice, an intervention in the form of a therapy element, an intervention in the form of outreach by a coach, any other suitable intervention, etc.) delivered through an application executing on a mobile computing device of a patient. Additionally or alternatively, an indication generated in previous blocks of the method 100 can be used to indicate trends in patient state, for instance, on a dashboard accessible to a caretaker of a patient (as described in further detail below). Additionally or alternatively, an indication generated based upon outputs of previous blocks of the method 100 can be used to trigger an action to be performed by the user (e.g., a patient action related to an exercise for improving health). As such, a patient's record on a dashboard, enhanced with trends in the patient's state, can be used to provide richer caretaker-patient interaction.

As noted above, Block S180 of the method 100 can contribute to improved efficiency in handling patients by enhancing delivery of patient-related indications to a healthcare provider, reducing volume of patient-related indications to the healthcare provider, and providing improved patient outcomes through an improved assessment of patient states of need. In transmitting the indications, Block S180 can include adapting to clinical workflow of a healthcare provider operation, wherein indications and/or suggested interventions (e.g., outreach) related to the indication(s) can be configured to reduce time needed to resolve a patient state associated with an indication. For instance, a suggested intervention resulting from Block S180 can include an intervention (e.g., health advice) characterized by low resource use (e.g., in terms of time, in terms of effort). Additionally or alternatively, a suggested intervention may indicate that a lower resource use intervention (e.g., phone call) is sufficient, in comparison to a higher resource use intervention (e.g., an in person visit), thus increasing efficiency of clinical workflow. Additionally or alternatively, timing of indication provision to the entity in Block S180 can contribute to interventions at more opportune times, such that the entity's resource use in intervening for a patient is optimized to have a maximum effect on the patient. In more detail, behavior-derived data components (e.g., from the passive dataset) can be used to identify better days in which to provide an intervention, and contextual data components (e.g., a location of the user) can be used to identify a better time at which to provide an intervention, based on the contextual data components. Furthermore, data components can be used to identify appropriate intervention categories. For instance, behavior-derived data components (e.g., data components indicative of lethargy) can be used to warrant an intervention focused on improving a level of activity of the user, and/or improving work-life balance associated with being at work after hours.

Thus, Block S180 functions to improve patient outcomes (e.g., to restore the patient to a healthy state) and to improve clinical efficiency (e.g., in reducing resource use/resource waste).

Figure 3A:
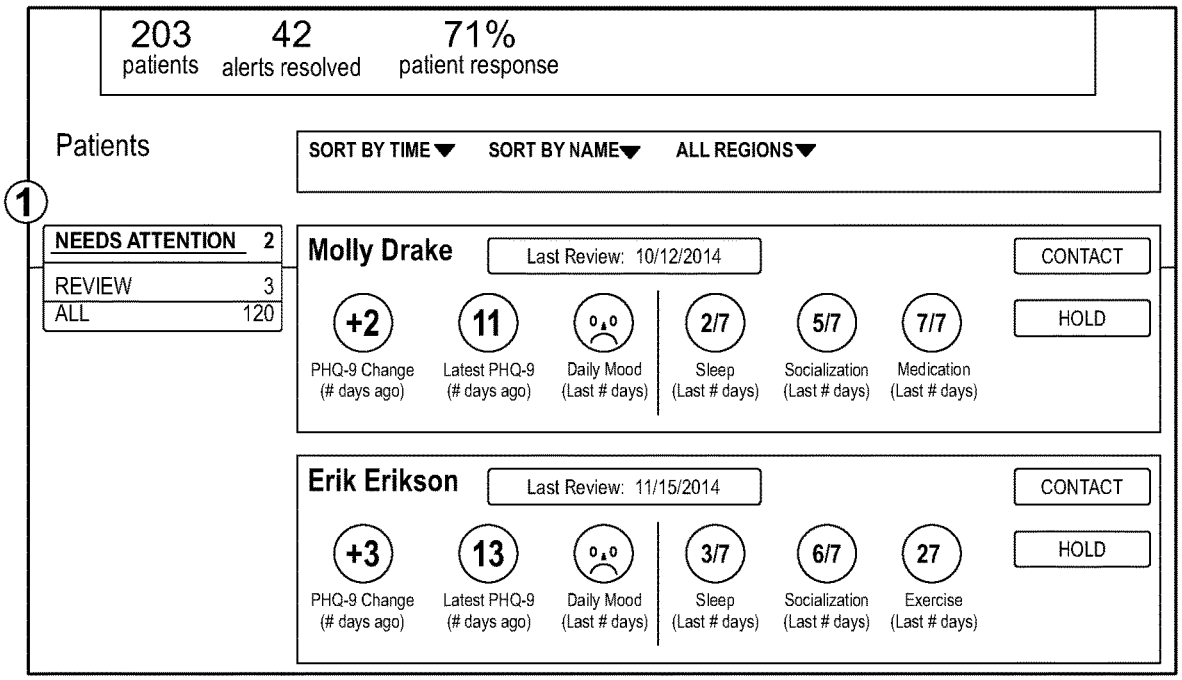
FIGS. 3A-3E depict examples of dashboards for providing indications in an embodiment of a method for providing patient indications to an entity.
Figure 3B:
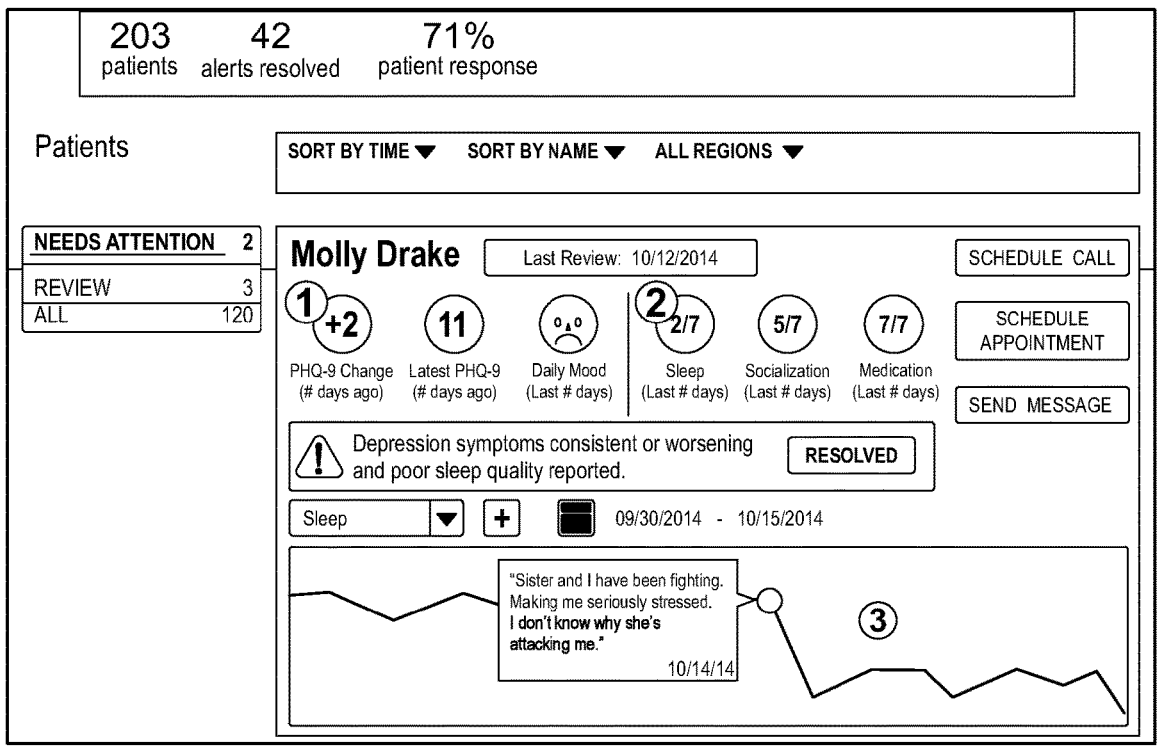
Figure 3C:
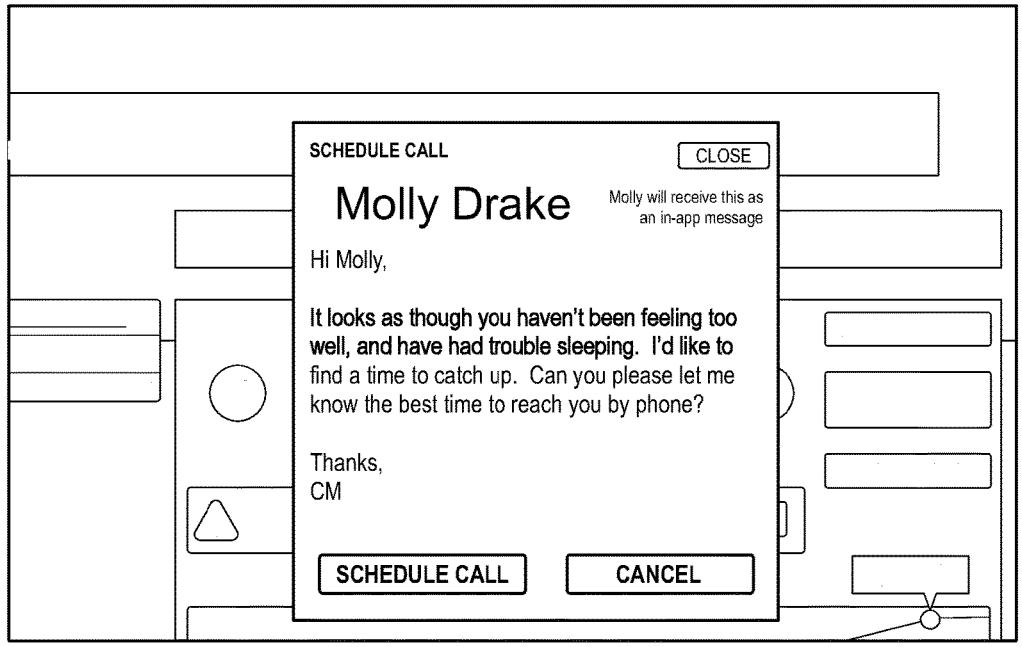
Figure 3D:
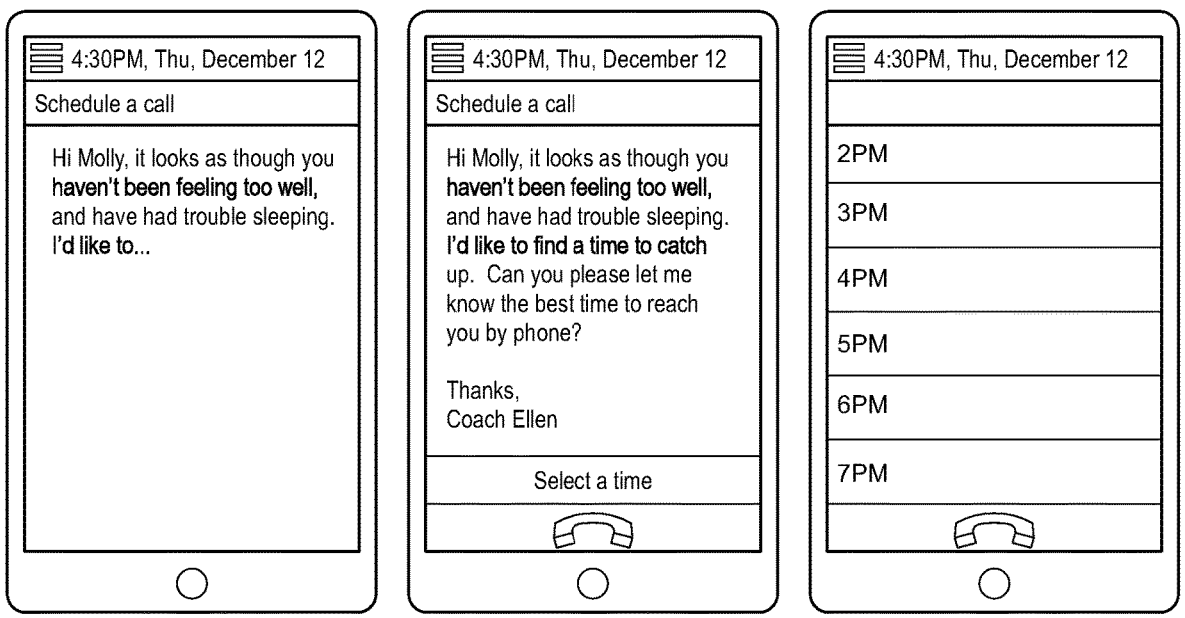

In the example shown in FIG. 3A, indication(s) of Block S180 can be provided at a dashboard of a web portal, wherein the indication(s) are text-based indications including the name(s) of the patient(s) associated with the indication(s) and the type(s) of the indication(s) (e.g., related to active data, related to behavioral heuristics data, related to predictive model-derived data, etc.). In the example shown in FIG. 3A, workflow-relevant parameters can also be presented to the entity, including a number of patients that the entity is responsible for, a number of indications resolved by the entity, a number of outstanding indications for the entity, flagged indications (e.g., indications requiring attention), a parameter associated with patient response, and a summary of other patient-related factors (e.g., as associated with sleep, socialization, medication adherence, exercise behavior, etc. determined from the predictive model). In the example shown in FIG. 3A, the dashboard can be configured to enable the entity to sort patients of the entity by name, time point of an associated indication, region, indication severity, and any other suitable factor. Furthermore, the dashboard can be configured to render trends in symptoms or indication severity of a patient (e.g., with a graph), as shown in FIG. 3B. As shown in FIGS. 3A, 3C, 3D, the dashboard can further be configured to enable the entity to perform an intervention action (e.g., schedule a call with a patient, schedule an appointment with a patient, send a message to a patient, etc.). Indication transmission in Block S180 can, however, be performed in any other suitable manner.

Figure 3E:
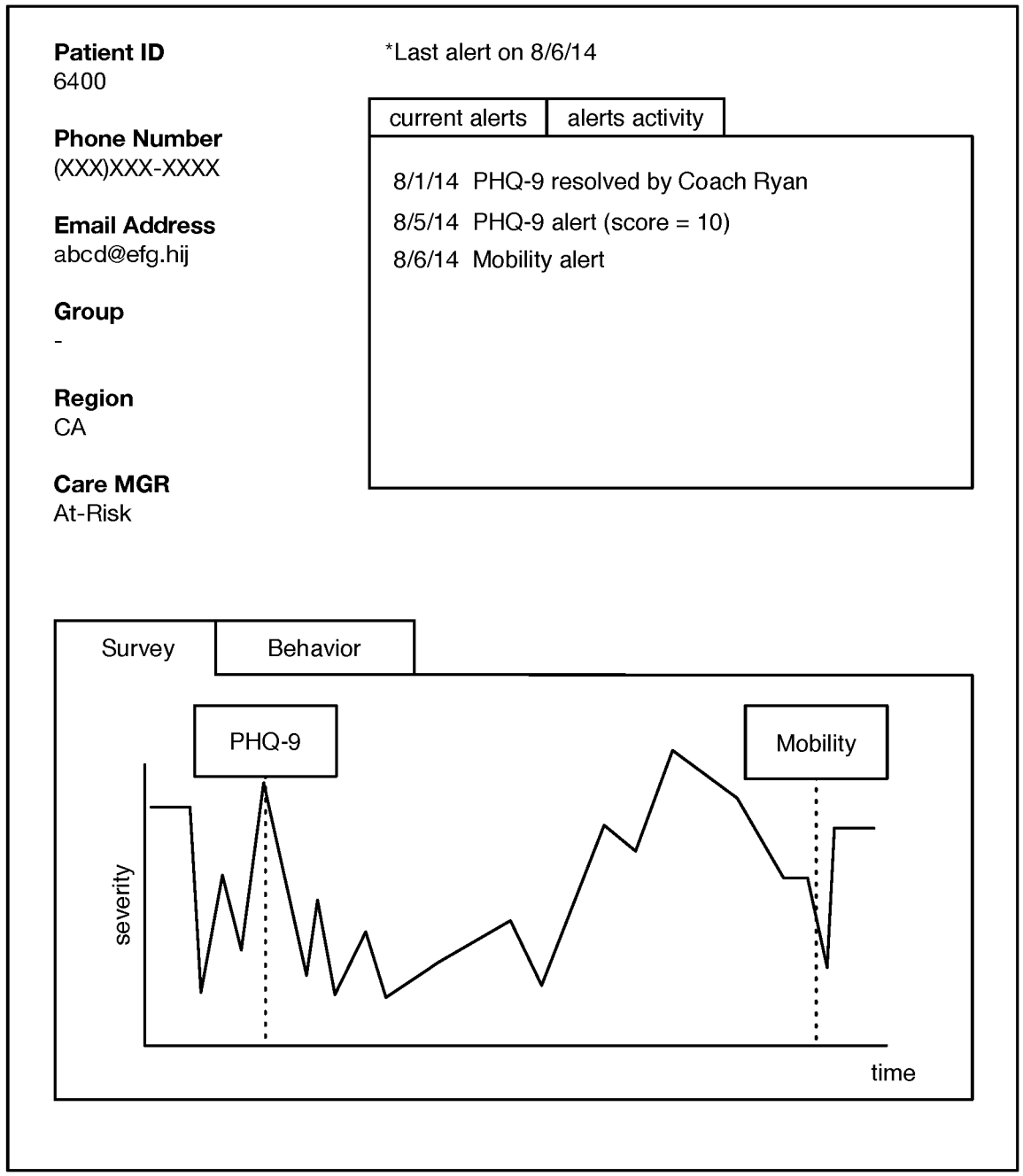

In another specific example, as shown in FIG. 3E, a dashboard can include a patient identification number, contact information of the patient (e.g., phone number, email address, etc.), a categorization of the patient (e.g., within a patient group, as an at-risk patient, etc.), a location of the patient, current alerts/indications of the patient (e.g., a mobility-parameter-related alert, a PHQ-9 score related alert, etc.), a status of each current alert/indication of the patient (e.g., unresolved, resolved, entity associated with resolution of the alert, etc.), historical alert/indication activity, the time at which the last alert/indication occurred, a timeline of events of the patient (e.g., displayed as a graph)

that includes trends of survey responses of the patient, passive data-related indications of the patient, active-data related indications of the patient, predictive model-related indications of the patient, and any other suitable behavioral data-related information relevant to the patient's health.

Figure 5:
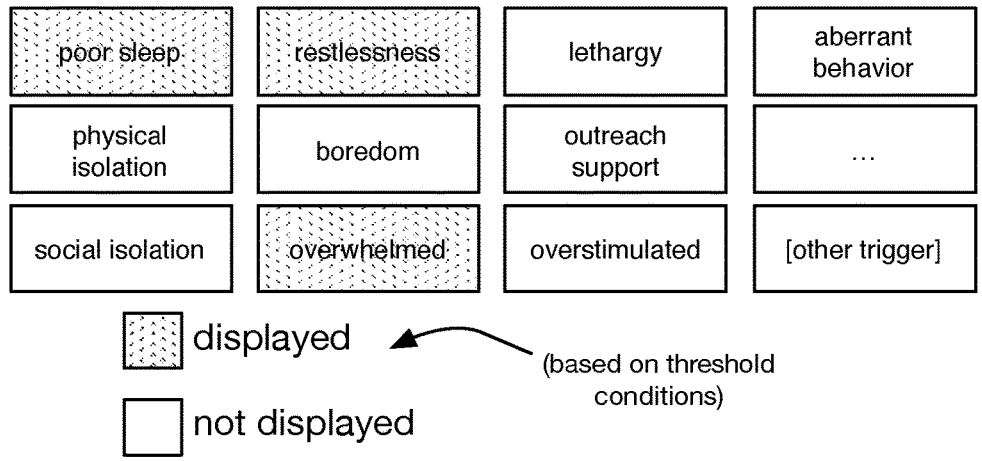
FIG. 5 depicts an example of a portion of an embodiment of a method for providing patient indications to an entity.
Figure 5:
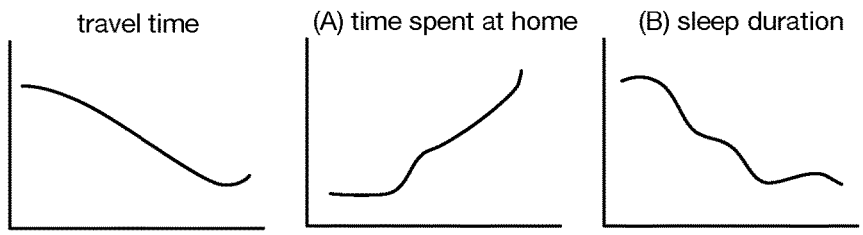
Figure 5:
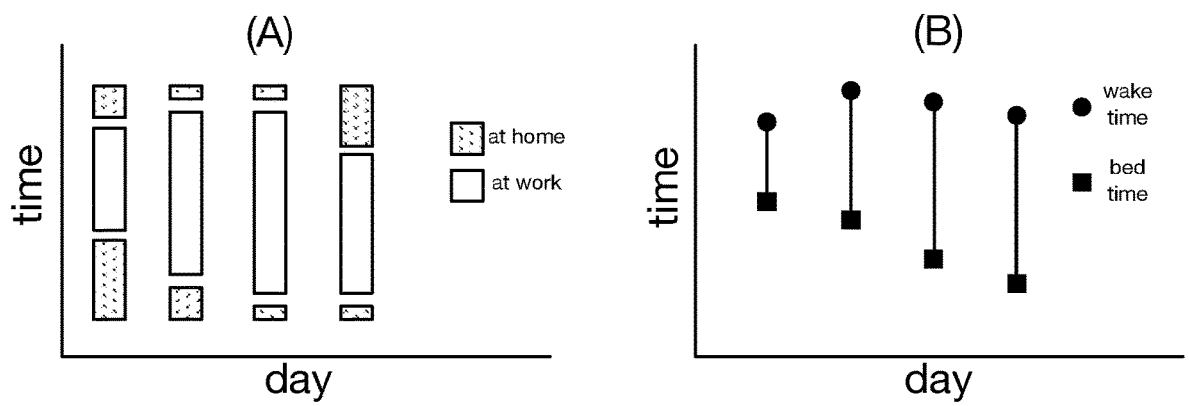

In another specific example, as shown in FIG. 5, a dashboard can include: (in addition to or in alternative to above elements) selected triggers associated with a patient for display to an entity (e.g., based on satisfaction of threshold conditions associated with each trigger); trends in selected behaviors of the patient associated with the triggers; and other visualizations of behaviors of the patient, in coordination with trends in behavior of the patient.

In association with the dashboard described above, Block S180 can include providing an entity (e.g., coaching entity, listening entity, other therapeutic entity, etc.) with a patient population tool within a software application, wherein the patient population tool summarizes key information of each of a population of patients associated with the entity. In a first specific example, as shown in FIG. 3F, the patient population tool can include: a list of all patients associated with the entity (e.g., with user identification codes); indication of exhibition of suicidal ideation for each individual (e.g., number of instances of suicidal ideation); active outreach needs of each individual; a number of days associated with active outreach for each individual; outreach priority for each individual; number of unread messages for each individual; a duration of time since the last message was sent to each individual; and a selectable link that allows the entity to establish communication with the patients by phone call and/or text-based messaging.

In variations of the example described above, as shown in FIG. 3G, the patient population tool can further include features that allow the entity to retrieve additional information for each of the population of patients. As such, Block S180 can include: in response to the entity hovering over an outreach-related tab associated with a specific patient, providing the entity with PHQ-9 score information for the specific patient (e.g., an indication of changes in score, raw score value, date of most recent PHQ-9 survey, etc.). Additionally or alternatively, as shown in FIG. 3H (top left), Block S180 can include: in response to the entity selecting a tab associated with a specific patient, retrieving and presenting a chat window to the entity within a software application, wherein the chat window includes a field for historical chats between the patient and the entity, a field for the entity to input new chats, and a set of action-options that allow the entity to perform an action (e.g., sharing of health-related content with the patient, sending of a survey to the patient, adding of a reminder to a calendar of the patient, indicating completion of outreach for a patient, archiving of a chat with the patient, etc.) related to care of the patient.

Additionally or alternatively, as shown in FIG. 3, Block S180 can include: in response to the entity selecting a menu expansion option associated with a specific patient, retrieving and presenting relevant notes and a summary of symptoms and activities associated with the patient to the entity, wherein the notes can include reminders provided to the patient, goals of the patient, contextual information of the patient (e.g., diagnoses, personal life events, medications, therapists of the patient, etc.), and wherein the summary can include: a list of symptoms of the individual (e.g., sleep, exercise, socialization, substance abuse, and functional impairment), along with an indication of the state of improvement of the symptom (e.g., worsening vs. improving, and indications of the source(s) from which the symptom states were determined or observed (e.g., from passive data, from predictive models, from survey data, from the coaching entity, etc.); trend in PHQ-9 scores; an indication of exhibition of suicidal ideation by the individual; a list of assigned and unassigned tasks (e.g., meditation task, mindfulness task, sensory awareness task, sleep improvement task, exercise task, etc.) to be completed by the individual, along with state of completion; and a list of health advice pieces viewed by the individual.

Additionally or alternatively, in the example shown in FIG. 3H (middle right and bottom left), Block S180 can include providing the entity with a library of content, where the entity can input search terms at a user input device, and retrieve appropriate health tips to provide to the patient, based on specific symptoms of the patient. However, Block S180 can include generation and/or provision of any other suitable tools and reports to the entity, some examples, variations, and embodiments of which are described in U.S. application Ser. No. 15/005,923 filed on 25 Jan. 2016 and entitled "Method for Providing Therapy to an Individual", which is herein incorporated in its entirety by this reference.

Figure 4:
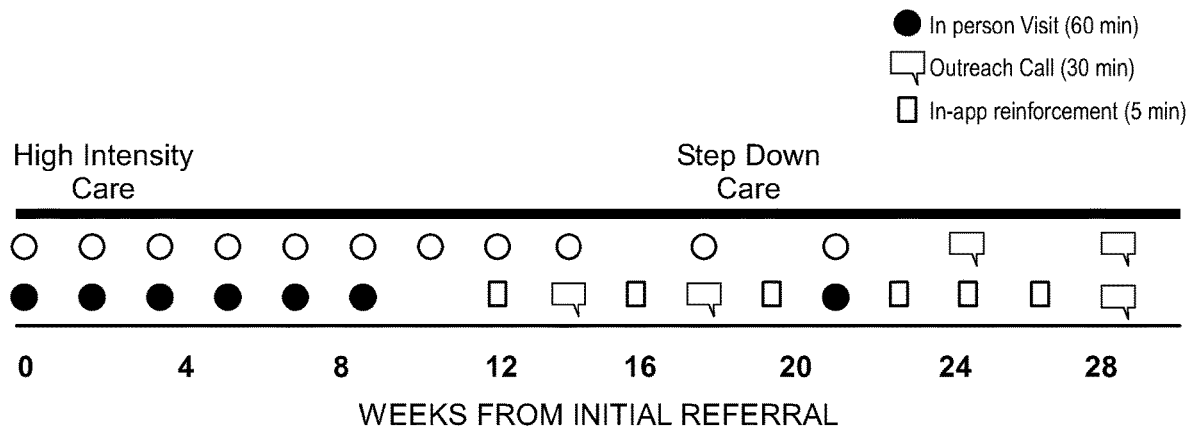
FIG. 4 depicts an example result of an embodiment of a method for providing patient indications to an entity.

The method 100 can, however, include any other suitable blocks or steps configured to provide patient indications to an entity. For instance, the method 100 can facilitate provision of interventions (e.g., an outreach phone call, an outreach text-based message, a health tip, a cognitive behavioral therapy based intervention, a clinical intervention, etc.) for patients requiring help. Additionally or alternatively, the method 100 can allow patients to be transitioned to a higher degree of care, and/or from a state of high intensity care to a state of step-down care (or maintenance care), thus increasing effectiveness of resource use, as shown in FIG. 4. In transitioning patients from a state of high intensity care to maintenance care, front-loading a period of indication transmission (associated with high resource use) pertaining to the patient, and then monitoring/maintaining patient state with low resource use interventions can allow the patient to use a smaller amount of resources. Additionally or alternatively, blocks of the method 100 can be used to identify patients who relapse into worse states of a condition, based upon monitoring of the patients. For instance, the method can 100 can include a repetition of blocks of the method at multiple periods in time, such that the method 100 can be used to monitor health of a population of patients over time. Thus, outputs of a first repetition of the method 100 for a first time period and outputs of a second repetition of the method 100 for a second time period can be used to generate a longitudinal analysis of health of each of a population of patients, such that trends in health of the population can be assessed and managed appropriately by way of one or more entities associated with the population.

Furthermore, as a person skilled in the art will recognize from the previous detailed description and from the figures and claims, modifications and changes can be made to the method 100 without departing from the scope of the method 100.

2. System

Figure 6:
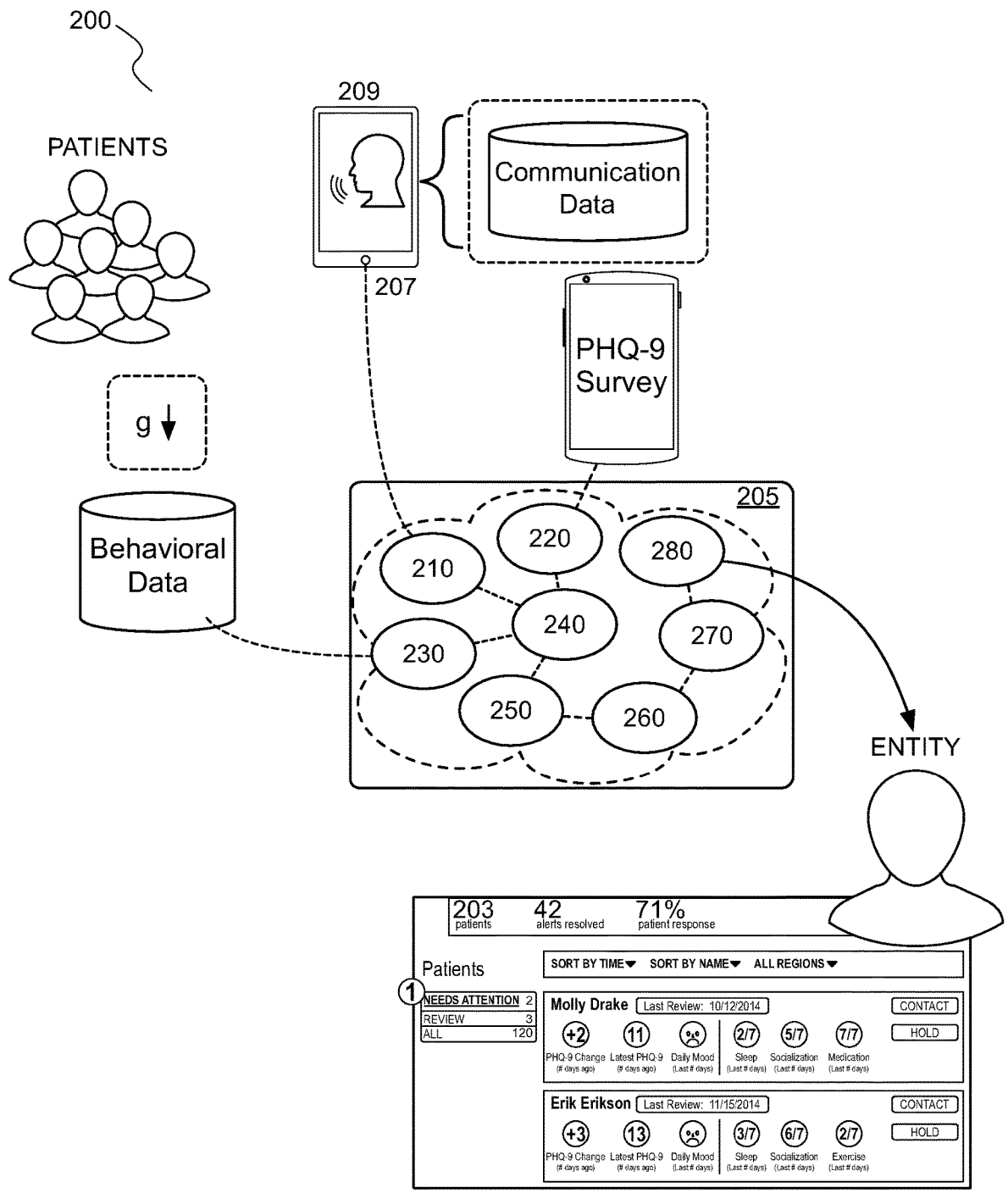
FIG. 6 depicts an embodiment of a system for providing patient indications to an entity.

As shown in FIG. 6, a system 200 for providing patient indications to an entity includes: a processing system 205 including: interfaces 207 with data collection applications executing on mobile computing devices 209 of a population of patients; a first module 210 configured to access a log of use of a communication application and a sensor signal processor module coupled to the data collection applications on the mobile computing devices; a second module 220 configured to receive a survey response dataset in association with a time period for each of the population of patients;

a third module 230 that generates a behavioral dataset, derived from the sensor signal processor module and the log of use, associated with the time period and derived from passive behavior; a fourth module 240 that generates a predictive model derived from at least one of the log of use, the survey response dataset, and the behavioral dataset; a fifth module 250 that generates a first comparison between the survey response dataset and a first threshold condition, a second comparison between the behavioral dataset and a second threshold condition, and a third comparison between an output of the predictive model and a third threshold condition; a sixth module 260 that generates an indication in response to at least one of the first, the second, and the third comparisons, thereby producing a set of indications corresponding to a subset of patients of the set of patients; a seventh module 270 that ranks the set of indications according to a severity factor; and an eighth module 280 that transmitting a portion of the set of indications to the entity according to a resource constraint of the entity.

Numbering? The system 200 functions to perform at least a portion of the method 100 described in Section 1 above, but can additionally or alternatively be configured to perform any other suitable method for providing patient indications to an entity. The system 200 is preferably configured to facilitate reception and processing of a combination of active data (e.g., inputs provided by individuals, post-communication survey responses) and passive data (e.g., unobtrusively collected communication behavior data, mobility data, etc.), but can additionally or alternatively be configured to receive and/or process any other suitable type of data. As such, the processing system 205 can be implemented on one or more computing systems including one or more of: a cloud-based computing system (e.g., Amazon EC3), a mainframe computing system, a grid-computing system, and any other suitable computing system. Furthermore, reception of data by the processing system 205 can occur over a wired connection and/or wirelessly (e.g., over the Internet, directly from a natively application executing on an electronic device of the individual, indirectly from a remote database receiving data from a device of the individual, etc.).

The processing system 205 and data handling by the modules of the processing system 205 are preferably adherent to health-related privacy laws (e.g., HIPAA), and are preferably configured to privatize and/or anonymize individual data according to encryption protocols. In an example, when an individual installs and/or authorizes collection and transmission of personal communication data by the system 200 through the native data collection application, the native application can prompt the individual to create a profile or account. In the example, the account can be stored locally on the individual's mobile computing device 209, in a process as shown in FIGS. 3B, D, and 7, and/or remotely. Furthermore, data processed or produced by modules of the system 200 can be configured to facilitate storage of data locally (e.g., on the patient's mobile computing device, in a remote database), or in any other suitable manner. For example, private health state-related data can be stored temporarily on the patient's mobile computing device in a locked and encrypted file folder on integrated or removable memory. In this example, the patient's data can be encrypted and uploaded to the remote database once a secure Internet connection is established. However, individual data can be stored on any other local device or remote data in any other suitable way and transmitted between the two over any other connection via any other suitable communication and/or encryption protocol. As such, the modules of the system 200 can be configured to perform embodiments, variations, and examples of the method 100 described above, in a manner that adheres to privacy-related health regulations.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of an individual computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for facilitating personalized treatment to a patient by an entity, the method comprising:

for each of a set of patients:
collecting a set of information comprising:
log of use information from a communication application, wherein the log of use information is associated with messages sent by the patient in the communication application;
receiving a survey response dataset provided by the patient;
generating a behavioral dataset, wherein the behavioral dataset is derived from the log of use information;
generating a predictive model for the patient, wherein the predictive model comprises a machine learning model trained on an initial set of training data associated with the patient;
generating a set of behavioral features derived from outputs of the predictive model and at least one of the behavioral dataset or the survey response dataset, wherein generating the set of behavioral features comprises calculating a physical isolation feature from GPS data;
generating a comparison between at least one of the set of behavioral features and a threshold condition;
producing a set of indications corresponding to the set of patients, the set of indications derived from generation of, for each of the set of patients, the comparison, the set of indications comprising an indication of exhibition of suicidal ideation;
in response to producing the set of indications, enabling a communicable link with a computing device of the entity; and
transmitting a portion of the set of indications to the entity according to a resource constraint of the entity by way of the communicable link, wherein transmitting the portion of the set of indications comprises:

generating a report based on the portion of the set of indications;

transmitting the report to the entity, wherein transmitting the report comprises rendering the report at a dashboard of an application accessible through a computing device of the entity, the dashboard observable at a display of the computing device, and wherein rendering the report at the dashboard includes rendering a visual representative of a behavioral feature of each patient associated with the portion of the set of indications; and automatically updating the predictive model based on the set of indications.

2. The method of claim 1, wherein the survey response dataset comprises a set of survey responses completed by the patient.

3. The method of claim 1, wherein the set of information further comprises sensor information from a sensor system, wherein the behavioral dataset is derived from the sensor information and the log of use information.

4. The method of claim 1, wherein the visual representative of a behavioral feature of each patient comprises at least one of:

a sleep duration of the patient for one or more of a set of days;

a time spent by the patient at a particular location; and a travel time of the patient.

5. The method of claim 1, wherein transmitting the portion of the set of indications further comprises generating and providing a patient population tool to the entity within an application accessible at a computing device of the entity.

6. The method of claim 5, wherein the patient population tool summarizes a list of all patients associated with the entity and at least one of:

an indication of exhibition of suicidal ideation for each individual;

an outreach priority for each individual;

a number of unread messages from the entity for each individual; and a selectable link that allows the entity to establish communication with each patient.

7. The method of claim 1, wherein the predictive model is further determined based on a second set of multiple patients.

8. The method of claim 1, wherein collecting the log of use information comprises extracting, from a log of use dataset, a communication parameter derived from at least one of: a number of text messages received and sent, a number of phone calls received and sent, a phone call duration, an incoming call count, and a number of ignored calls.

9. The method of claim 1, wherein the enabling of the communicable link is configured to facilitate a matching of the patient with the entity, wherein the matching of the patient with the entity is performed based at least in part on a resource constraint metric associated with the entity, wherein the resource constraint metric is determined based on at least one of a workflow volume associated with the entity or an experience level associated with the entity.

10. A method for facilitating personalized treatment to a patient by an entity, the method comprising:

for the patient:

collecting a set of information comprising:

log of use information from a communication application, wherein the log of use information comprises messages sent by the patient in the communication application;

receiving a survey response dataset provided by the patient, wherein the survey response dataset is completed by the patient;

generating a behavioral dataset, wherein the behavioral dataset is derived from the log of use information;

generating a set of behavioral features from the behavioral dataset, wherein generating the set of behavioral features comprises calculating a physical isolation feature from GPS data;

generating a predictive model for the patient, wherein the predictive model comprises a machine learning model trained on an initial set of training data associated with the patient;

generating a set of comparisons, the set of comparisons comprising at least one of:

a first comparison between the survey response dataset provided by the patient and a first threshold condition;

a second comparison between the behavioral dataset and a second threshold condition; and a third comparison between an output of the predictive model and a third threshold condition;

producing an indication corresponding to the patient, the indication generated based on the set of comparisons;

in response to producing the indication, enabling a communicable link with a computing device of the entity;

transmitting the indication to the entity by way of the communicable link; and automatically updating the predictive model based on the indication.

11. The method of claim 10, wherein collecting the log of use information further comprises extracting, from a log of use dataset, a communication parameter derived from at least one of: a number of text messages received and sent, a number of phone calls received and sent, a phone call duration, an incoming call count, and a number of ignored calls.

12. The method of claim 11, further comprising generating a report based on the indication and transmitting the report to the entity, wherein transmitting the report includes rendering the report at a dashboard of an application accessible through a computing device of the entity, the dashboard observable at a display of the computing device.

13. The method of claim 10, wherein the set of comparisons comprises the first comparison, wherein the first comparison is determined based on a set of responses from the patient in the survey response dataset completed by the patient.

14. The method of claim 10, wherein the predictive model is derived from at least one of the survey response dataset and the behavioral dataset.

15. The method of claim 10, wherein the set of comparisons comprises the first comparison, the second comparison, and the third comparison.

16. The method of claim 15, further comprising aggregating a set of outputs, wherein the set of outputs are produced based on each of the first, second, and third comparisons.

17. The method of claim 16, wherein aggregating the set of outputs comprises weighting the set of outputs.

18. The method of claim 10, wherein the predictive model is further determined based on a set of multiple patients.

19. The method of claim 10, wherein the enabling of the communicable link is configured to facilitate a matching of the patient with the entity, wherein the matching of the patient with the entity is performed based at least in part on a resource constraint metric associated with the entity, wherein the resource constraint metric is determined based on at least one of a workflow volume associated with the entity or an experience level associated with the entity.

\* \* \* \* \*